US010980859B2

(12) United States Patent
Hu et al.

(10) Patent No.: US 10,980,859 B2
(45) Date of Patent: Apr. 20, 2021

(54) IN VIVO INDIVIDUALIZED SYSTEMIC IMMUNOTHERAPEUTIC METHOD AND DEVICE

(71) Applicant: Hangzhou Converd Co., Ltd., Zhejiang (CN)

(72) Inventors: Fang Hu, Zhejiang (CN); Ronghua Zhao, Zhejiang (CN); Siyi Chen, Zhejiang (CN); Bo Wu, Zhejiang (CN); Huiqun Xia, Zhejiang (CN); Yanjun Zheng, Zhejiang (CN)

(73) Assignee: Hangzhou Converd Co., Ltd., Zhejiang (CN)

( * ) Notice: Subject to any disclaimer, the term of this patent is extended or adjusted under 35 U.S.C. 154(b) by 674 days.

(21) Appl. No.: 15/058,456

(22) Filed: Mar. 2, 2016

(65) Prior Publication Data

US 2016/0250292 A1     Sep. 1, 2016

Related U.S. Application Data

(63) Continuation-in-part of application No. PCT/CN2014/085287, filed on Aug. 27, 2014.

(30) Foreign Application Priority Data

Sep. 2, 2013   (CN) .......................... 201310392618.2

(51) Int. Cl.
| | | |
|---|---|---|
| *A61K 38/19* | (2006.01) | |
| *A61K 35/761* | (2015.01) | |
| *A61K 45/06* | (2006.01) | |
| *A61K 31/513* | (2006.01) | |
| *A61K 31/7068* | (2006.01) | |
| *A61K 31/704* | (2006.01) | |
| *A61K 33/24* | (2019.01) | |
| *A61K 31/475* | (2006.01) | |
| *A61K 35/768* | (2015.01) | |
| *A61K 38/48* | (2006.01) | |
| *A61K 35/763* | (2015.01) | |
| *A61K 35/74* | (2015.01) | |
| *A61K 38/55* | (2006.01) | |
| *A61K 35/766* | (2015.01) | |
| *C07K 16/28* | (2006.01) | |

(Continued)

(52) U.S. Cl.
CPC .......... *A61K 38/193* (2013.01); *A61K 31/475* (2013.01); *A61K 31/513* (2013.01); *A61K 31/704* (2013.01); *A61K 31/7068* (2013.01); *A61K 33/24* (2013.01); *A61K 35/74* (2013.01); *A61K 35/761* (2013.01); *A61K 35/763* (2013.01); *A61K 35/766* (2013.01); *A61K 35/768* (2013.01); *A61K 38/191* (2013.01); *A61K 38/4873* (2013.01); *A61K 38/55* (2013.01); *A61K 39/3955* (2013.01); *A61K 45/06* (2013.01); *C07K 16/2803* (2013.01); *C07K 16/2818* (2013.01); *C07K 16/2827* (2013.01); *C07K 16/30* (2013.01); *C12N 7/00* (2013.01); *A61K 2039/505* (2013.01); *A61K 2039/507* (2013.01); *C07K 2317/76* (2013.01); *C12N 2710/10332* (2013.01); *Y02A 50/30* (2018.01)

(58) Field of Classification Search
CPC ........ C12N 2710/10332; A61K 35/761; A61K 38/193; A61K 35/768; A61K 2039/505; C07K 2317/76; C07K 16/2803; C07K 16/2827

See application file for complete search history.

(56) References Cited

U.S. PATENT DOCUMENTS

| 5,677,178 A | 10/1997 | McCormick |
| 2004/0146488 A1* | 7/2004 | Hu .......................... A61K 35/74 424/93.2 |

(Continued)

FOREIGN PATENT DOCUMENTS

| CN | 1412295 A | 4/2003 |
| CN | 1110553 C | 6/2003 |

(Continued)

OTHER PUBLICATIONS

Kurane et al (Annals of Surgical Oncology, 1997, vol. 4, pp. 579-585) (Year: 1997).*
Saffran et al (Cancer Gene Therapy, 1998, vol. 5, pp. 321-330). (Year: 1998).*
Melcher et al (Molecular therapy, 2011, vol. 19, pp. 1008-1016) (Year: 2011).*
Biedereretal (Journal of Molecular Medicine, 2002, vol. 80, pp. 163-175). (Year: 2002).*
Livraghi et al (Cancer, 1998, vol. 83, pp. 48-57). (Year: 1998).*
Hargadon et al, International Immunopharmacology, 2018, vol. 62, pp. 29-39 (Year: 2018).*

(Continued)

Primary Examiner — Karen A. Canella
(74) Attorney, Agent, or Firm — The Webb Law Firm

(57) ABSTRACT

The invention provides an in vivo individualized systemic immunotherapeutic method and device. The method includes, in a non-sequential manner: (1) increasing release amount of tumor antigens at a tumor site; (2) at the tumor site, increasing level of proteins capable of adhering to and/or wrapping the tumor antigens; (3) at the tumor site, increasing level of dedicated antigen-presenting cells involved in immunity, and establishing, between the dedicated antigen-presenting cells and immune effector cells, a close connection capable of activating the immune effector cells; and (4) at the tumor site, increasing level and improving function of the immune effector cells. The steps (1)-(4) each reaches a maximum value at a respective time which overlaps with each other maximally, as well as at a respective site which overlaps with each other maximally. The invention combines oncolytic therapy and immunotherapy, in individualized systemic immunotherapy, and provides significantly improved therapeutic effect.

9 Claims, 15 Drawing Sheets

(51) Int. Cl.
*A61K 39/395* (2006.01)
*C07K 16/30* (2006.01)
*C12N 7/00* (2006.01)
*A61K 39/00* (2006.01)

(56) References Cited

U.S. PATENT DOCUMENTS

| | | | |
|---|---|---|---|
| 2004/0202663 A1* | 10/2004 | Hu | A61K 38/191 424/155.1 |
| 2005/0214923 A1* | 9/2005 | Yu | A61K 48/005 435/235.1 |
| 2011/0287057 A1 | 11/2011 | Podack | |
| 2012/0009140 A1 | 1/2012 | Godfrin et al. | |
| 2012/0100182 A1 | 4/2012 | Mooney et al. | |
| 2012/0128656 A1 | 5/2012 | Har-Noy | |
| 2014/0377221 A1* | 12/2014 | Tufaro | G01N 33/57484 424/85.2 |

FOREIGN PATENT DOCUMENTS

| CN | 1780632 A | 5/2006 | |
|---|---|---|---|
| CN | 1806849 A | 7/2006 | |
| CN | 101873862 A | 10/2010 | |
| CN | 102006891 A | 4/2011 | |
| CN | 102076359 A | 5/2011 | |
| CN | 102258772 A | 11/2011 | |
| CN | 102883746 A | 1/2013 | |
| WO | WO2013/043647 | * | 3/2013 |

OTHER PUBLICATIONS

Fang et al., "Soluble tumor body individualized tumor vaccine induced preliminary clinical trials for the treatment of malignant tumor", China Academic Journal Electronic Publishing House, 2004, pp. 244-252, English-language Abstract attached.

Song, "Animal Experimental Study on Combined Immunization of Mice with Tumours by Mixed Hsps/Peptide Combination Vaccine, Interleukin 12 and Low Dose Cyclophosphamides", China Doctoral Dissertations Full-Text Database, 2007, ISSN: 1674-022X.

Zheng et al., "Effect of interferon gamma and heat-shock treatment on expressions of MHC class I and HSP70 in glioma cells", Chinese Journal of Minimally Invasive Neurosurgery, 2009, vol. 14:10, ISSN: 1009-122X.

* cited by examiner

IN VIVO INDIVIDUALIZED SYSTEMIC IMMUNOTHERAPEUTIC METHOD AND DEVICE

CROSS-REFERENCE TO RELATED APPLICATIONS

The present application is a continuation-in-part of PCT Application No. PCT/CN2014/085287, filed on Aug. 27, 2014, which claims the benefit of Chinese patent application No. 201310392618.2, filed on Sep. 2, 2013, the disclosures of which are incorporated herein by reference in their entireties.

FIELD OF THE INVENTION

The present invention relates to the field of biomedicine, and particularly to an anti-tumor therapeutic method and device.

BACKGROUND OF THE INVENTION

The advances in medical sciences are giving impetus to researches on therapeutic methods for tumors, which are no longer limited to the routine therapies. The routine anti-tumor therapies include the conventional therapies such as surgery, radiotherapy, chemotherapy, and hyperthermia therapy, and also, a growing number of targeted therapies which have been developed successfully in recent years, and each of these therapies can be used solely or in combination with other therapies in the practice. However, heterogeneity in tumors of the same type has been neglected in the conventional therapies, resulting in ineffective treatment for some patients; and some patients have to discontinue their treatment because of toxicity or side-effects of these therapies; besides, tumor resistance to therapeutic agents due to cellular adaptations is hard to overcome in these routine therapies, and tumor recurrence and metastasis often occur after treatment. As to recently developed targeted tumor therapies, although their advantages include precise targets for treatment and less toxicities or side effects, they provide no benefit in treating tumors being independent of the relevant targets or tumors with cellular adaptive resistance after initial therapy. Therefore, tumor therapies specific for individual tumors with fewer toxicities or side effects and greater effectiveness are needed.

With the advances in molecular pathology of tumors and knowledge of the relationship between genetic alterations and disease, biological therapies for tumors have been developed. At present, the biological therapies for tumors mainly include immunotherapy and gene therapy for tumors.

Tumor immunotherapy refers to a variety of therapeutic strategies designed to induce the patient's own immune system to fight cancer. Currently, there exist some strategies with which lysis of tumor cells can be carried out in vitro and DCs (dendritic cells) are sensitized by tumor cell lysate, and then the DCs loaded with individual tumor-specific antigens will be infused back into the patient to induce or improve anti-tumor effect of the immune system, resulting in inhibition of tumor growth or remission of tumor, as well as a long-term protective immune response, thus effective treatment of the tumor can be achieved. For instance, Antigenics Inc. in USA has developed an individualized cancer vaccine, HSP (heat shock protein)-tumor peptide complex, based on the mechanisms of immunotherapy. The therapeutic procedures include: surgical removal of the tumor; isolation of tumor-derived HSP-tumor peptide complex from the removed tumor tissue; injection of the HSP-tumor peptide complex back into the patient to treat the tumor. However, since the spectrum of mutations in each individual's tumor varies significantly, a vaccine derived from a patient's tumor and prepared in vitro has to be applied to the same patient in the practice; it is not a broad spectrum vaccine which can be used for a lot of patients. Therefore, this immunotherapy cannot become a widely used treatment in the clinic; besides, preparation of such cancer vaccine involves strict procedures of extraction and synthesis in vitro, which is cumbersome and time-consuming and thus further limits the application of this immunotherapy.

Further studies on anti-tumor therapies have shown that the process of anti-tumor immune responses in vivo can be simulated through a systematic combination therapy. The combination of low-dose chemotherapy with immunotherapy is one of the existing strategies for tumor treatment. For example, the combination of chemotherapy and the immunotherapeutic agents like thymopentin and IL-2 (interleukin-2) is used to synergistically treat colon cancer; the combination of chemotherapy and the immunotherapeutic agents like GM-CSF (granulocyte-macrophage colony-stimulating factor), IL-2 and IFN-α (interferon alfa) is used to synergistically treat melanoma. Although these combination of chemotherapy and immunotherapy have shown some improved effectiveness against tumors, they fail to completely target various main aspects of the anti-tumor immune responses in vivo and also fail to take into account phase differences (time to peak values) among various stages of the immune response and the related overlapping effect, so the therapeutic effect is still not satisfactory when these combination therapies are used in the practice.

Oncolytic viruses are also used as one of the prior strategies for the treatment of tumors (oncolytic viral therapy). This therapeutic approach mainly utilizes the mechanism that oncolytic viruses can selectively replicate within tumor cells and cause tumor cell lysis to treat tumors.

An oncolytic virus, ONYX-015, was disclosed in U.S. Pat. No. 5,677,178. ONYX-015 is a specific oncolytic adenovirus constructed with a deletion of E1B-55KD gene region in the DNA sequence of human wild-type adenovirus type 5. ONYX-015 causes no harm to normal cells, but can selectively replicate and proliferate in tumor cells, causing lysis of these cells. The clinical trials of ONYX-015 for treatment of malignant tumors were started in 1996 in subjects with tumors such as head and neck tumors, glioma, pancreatic cancer, primary liver and gallbladder cancer, hepatic metastases from colorectal cancer, non-small cell lung cancer and cervical carcinoma, and the results indicated that this oncolytic virus is certainly effective and quite safe.

Another oncolytic virus, H101 (CCTCC Deposit No. V98003), was disclosed in Chinese patent No. CN1110553C. H101 is an oncolytic adenovirus obtained by genetic recombination of human adenovirus type 5 (Ad5) using genetic engineering techniques, in which E1B-55KD and E3-19KD gene were deleted, mainly. H101 can selectively replicate in tumor cells and contribute to cell lysis, so that effective oncolytic effect can be achieved. H101 was approved by CFDA for sale in China in 2006, and the New Drug Application (NDA) No. is Guo Yao Zhun Zi S20060027.

The oncolytic adenovirus, H101, was not only used as a sole therapy but also used in combination with chemotherapy for treatment of tumors in clinical trials thereof. In the combination therapies, the chemotherapeutic agents can be Gemzar, Vinorelbine (NVB), Cisplatin (CDDP), Adriamycin, 5-Fu (5-fluorouracil), and the like. These chemotherapeutic agents kill tumor cells by damaging the DNA of the cells through various mechanisms of action. Among which, one of the hydrolysis products of cisplatin, $[Pt(NH_3)_2(H_2O)_2]^{2+}$, can react with DNA to form chelates, thereby changing DNA's function when serving as a template; adriamycin can insert into DNA and inhibit DNA polymerase activity, so as to interfere with DNA replication and transcription; 5-FU can be converted into 5-fluorodeoxyuridine monophosphate (5F-dUMP) in human body, thereby blocking the methylation of deoxyuridine monophosphate (dUMP) to deoxythymidine monophosphate (dTMP) and further inhibiting the synthesis of DNA. The oncolytic adenovirus H101 achieves its therapeutic effect through massive viral replication in tumor cells which interferes with host cell functions, and it is a cell-cycle nonspecific agent. Therefore, from the perspective of the mechanism of anti-cancer drugs, synergistic effect can be expected when H101 is combined with the aforementioned chemotherapeutic agents. Furthermore, the results of the studies on oncolytic adenoviruses indicated that the chemotherapeutic agents such as Cisplatin and 5-FU did not interfere with the replication of the virus. Therefore, theoretically, it is appropriate to combine the oncolytic adenovirus H101 with chemotherapeutic agents to treat tumors in clinical practice. The clinical trials of this type of combination therapy also indicate that its anti-tumor efficacy is significantly improved compared to sole chemotherapy.

The results of the aforementioned clinical trials also indicate that there is a significant correlation between the efficacy of the oncolytic adenovirus and the patient's body temperature when treating tumor using the oncolytic adenovirus. That is to say, the therapeutic effect is significantly improved in patients with fever compared to patients without fever, whether the oncolytic adenovirus is used solely or in combination with chemotherapeutic agents. For example, when the therapy targeted superficial lesions of the body, a therapeutic response was achieved in 81.3% of patients with fever and in 78.1% of patients without fever; and similar results were also observed in a study regarding metastatic sites, in which a therapeutic response was achieved in 25.0% of patients with fever and in 6.3% of patients without fever.

In addition, some correlation was observed between the efficacy of an oncolytic adenovirus and the presence of heat shock proteins (HSPs), that is, the efficacy of the oncolytic adenovirus will be improved when massive expression of HSP occurs. Therefore, in clinical practice, the simultaneous application of topical heat to the tumor sites where H101 is injected will induce the local expression of endogenous HSPs and significantly enhance the local efficacy of H101, and a favorable therapeutic effect can also be achieved in the tumor sites where H101 is not injected. Alternatively, an inducible heat shock protein 70 (HSP70) gene sequence can be inserted into the genome of the reconstructed specific oncolytic adenoviruse, so that massive expression of HSP70 will be occurring along with viral replication and oncolysis. With these approaches, not only will the tumors injected with H101 shrink, but the metastases at distant sites will also be affected.

Although the strategies for the treatment of tumors in the prior art have been widely used in the clinical practice, for instance the applications of immune checkpoint inhibitors, cell therapy or bispecific antibodies, these anti-tumor therapies don't effectively combine radiotherapy, chemotherapy, oncolytic therapy, immunotherapy and etc. They only act on single target, single step of adaptive immunity and/or need complicated ex vivo examination and thus fail to systemically target various aspects of the anti-tumor immune responses in vivo, including antigen releasing, DC maturing, and activation of CTL (cytotoxic T lymphocyte), and also fail to take into account the overlapping effect of the peak values (maximum values) of the various aspects of the immune responses. Therefore, no satisfactory therapeutic effect can be achieved with these anti-tumor strategies. Our invention presents the systemic solution for that.

SUMMARY OF THE INVENTION

In order to overcome the above mentioned challenges, the present invention aims to provide a therapeutic method for the treatment of tumors, which is able to improve the anti-tumor therapeutic effect and enhance the individual-specific immune responses to various tumor antigens, so that it can be used in most tumor patients.

In one aspect, the present invention provides a therapeutic method for tumor treatment, which is an in vivo individualized systemic immunotherapeutic method, comprising, in a non-sequential manner, steps of:
(1) increasing release amount of tumor antigens at a tumor site where treatment is required in a tumor patient;
(2) at the tumor site, increasing level of proteins capable of adhering to and/or wrapping the tumor antigens;
(3) at the tumor site, increasing the level of the dedicated antigen-presenting cells involved in immunity, and establishing, between the dedicated antigen-presenting cells and immune effector cells, a close connection capable of activating the immune effector cells; and
(4) at the tumor site, increasing level and improving function of the immune effector cells, thus establishing a close connection between the immune effector cells and target cells, resulting in killing of the target cells; and wherein the release amount of the tumor antigens in step (1), the level of the proteins capable of adhering to and/or wrapping the tumor antigens in step (2), the level of the dedicated antigen-presenting cells involved in immunity and the close connection between the dedicated antigen-presenting cells and the immune effector cells in step (3), and the level and function of the immune effector cells in step (4) each reaches a maximum value at a respective time which overlaps with each other maximally, as well as at a respective site which overlaps with each other maximally.

In one embodiment of the present invention, the proteins capable of adhering to and/or wrapping the tumor antigens can be recognized by the dedicated antigen-presenting cells, or are expressed on the dedicated antigen-presenting cells.

In the above method of the present invention, the step for increasing the release amount of tumor antigens at a tumor site can be achieved by multiple approaches, such as applying an oncolytic agent to said tumor site; applying absolute ethyl alcohol, acetic acid, hot saline water, hot distilled water, or other agent which can induce tumor cell necrosis to said tumor site; applying radiofrequency ablation, microwave coagulation, high intensive focused ultrasound, laser-thermia, cryotherapy, or other treatment that can kill tumor cells to said tumor site.

In a preferred embodiment, an oncolytic agent is applied to the tumor site to increase the release amount of tumor antigens. The oncolytic agent includes an oncolytic microorganism, and the oncolytic microorganism includes oncolytic virus and oncolytic bacterium, and the oncolytic virus includes oncolytic adenovirus, oncolytic herpes simplex virus, oncolytic vesicular stomatitis virus, oncolytic newcastle disease virus, oncolytic poliovirus, oncolytic EB virus, and other oncolytic virus that can selectively replicate in tumor cells; the oncolytic bacterium includes oncolytic

*salmonella typhosa*, oncolytic *bifidobacterium*, oncolytic *Shigella*, oncolytic *Listeria*, oncolytic *bacillus pestis*, and other oncolytic bacteria that can selectively grow in tumor cells. The oncolytic agent can also comprise nucleic acid sequence which can encode pro-apoptotic gene, cytolytic gene, tumor necrosis factor gene, cysteine proteinase gene, γ-globulin gene, HA-1 antitrypsin gene, and other gene that plays a role in oncolysis.

Preferably, said proteins capable of adhering to and/or wrapping the tumor antigens are selected from MHC I, MHC II and heat shock proteins.

Heat shock proteins can be recognized by the dedicated antigen-presenting cells. The heat shock proteins include heat shock protein 70, heat shock protein 30, heat shock protein 60, heat shock protein 90, heat shock protein 94, heat shock protein 96, heat shock protein 110 and other types of heat shock proteins.

The level of heat shock proteins at the tumor site can be increased by applying topical stimulation at said tumor site. The stimulation includes heat, hypoxia, chill, infection, radiation, alcohol and other type of stimulation which can induce cells to produce heat shock protein.

Preferably, the level of heat shock proteins at the tumor site is increased by application of topical heat to said tumor site such that the topical temperature is 1-7° C. higher than the patient's normal body temperature.

In a preferred embodiment, the step for increasing the release amount of tumor antigens at a tumor site is performed prior to the step for increasing the level of proteins capable of adhering to and/or wrapping the tumor antigens at a tumor site.

In the above method of the present invention, the increase of the level of the dedicated antigen-presenting cells involved in immunity and the establishment of the close connection, between the dedicated antigen-presenting cells and the immune effector cells, capable of activating the immune effector cells at said tumor site can be achieved by regulation of the cytokines and chemokines which can inhibit or enhance the interaction between the dedicated antigen-presenting cells and the immune effector cells. The connection between the dedicated antigen-presenting cells and the immune effector cells includes the binding between major histocompatibility complexes (MHC) and T cell receptors, that is, an immunological synapse (IS). The dedicated antigen-presenting cells include dendritic cells, macrophages and specific B cells. The immune effector cells include $CD8^+$ cytotoxic T cells and $CD4^+$ T helper cells. The cytokines and chemokines which can enhance the interaction between dedicated antigen-presenting cells and the immune effector cells include TGF beta, IL1, IL6, IL-12, IL18; immune co-stimulation molecules, CD28, ICOS, 4-1BB, CD27, CD70, NKp30, CD137, GITR, and OX40. The cytokines and chemokines which can inhibit the interaction between the dedicated antigen-presenting cells and the immune effector cells include BTLA, KIR, LAG-3, TIM-3, A2aR, CTLA4, PD1 and PD-L1. Methods for regulating the expression and function of the above cytokines and chemokines include application of the related monoclonal antibodies or chemical compounds.

In the above method of the present invention, the increase of the level of the immune effector cells and the improvement of the function thereof at the tumor site, and establishment of the close connection between the immune effector cells and the target cells (namely, formation of an IS between the immune effector cells involved in immunity and the target cells of tumor), resulting in killing of the target cells, are achieved by regulation of the cytokines and chemokines which can inhibit or enhance the interaction between the immune effector cells and the target cells. The IS formed between immune effector cells and target cells includes the binding between MHCs and T cell receptors. The immune effector cells include $CD8^+$ cytotoxic T cells and $CD4^+$ T helper cells. The cytokines and chemokines which can enhance the interaction between the immune effector cells and the target cells include TGF beta, IL1, IL6, IL-12, IL18; immune co-stimulating factors, CD28, ICOS, 4-1BB, CD27, CD70, NKp30, CD137, GITR, and OX40. The cytokines and chemokines which can inhibit the interaction between the immune effector cells and the target cells include BTLA, KIR, LAG-3, TIM-3, A2aR, CTLA4, PD1 and PD-L1. Methods for regulating the expression and function of the above cytokines and chemokines include application of the related monoclonal antibodies or chemical compounds.

In the above method of the present invention, the increase of the level of the dedicated antigen-presenting cells involved in immunity and the increase of the level of the immune effector cells, and the improvement of the function thereof at said tumor site, can be achieved by administration of immunotherapeutic agents to patients. Preferably, the immunotherapeutic agents include interleukin-2, interleukin-3, interleukin-12, granulocyte/macrophage colony-stimulating factor (GM-CSF), thymosin, tumor necrosis factor (TNF), interferon (INF), chemotactic factors, levamisole, immune co-stimulation molecules, and other molecules that can boost immune responses.

Preferably, the method of the present invention comprises the steps of:
(i) applying oncolytic virus H101 to the tumor site for the step (1) and/or the step (2);
(ii) administrating GM-CSF to the tumor patient for the step (3);
(iii) administrating PD-L1 antibodies to the tumor patient for the step (4).

In a preferred embodiment, the therapeutic method of the present invention also includes the step of application of chemotherapy, radiotherapy and/or molecular targeting therapeutic agents for tumor in tumor patients. The chemotherapeutic agents include Vinorelbine, Cisplatin, Adriamycin, Gemzar, and 5-fluorouracil. Preferably, the step of the chemotherapy or radiotherapy is performed prior to step (1), (2), (3) and/or (4), especially when an oncolytic microorganism is applied to the tumor site to increase the release amount of tumor antigens. Further preferably, the step of chemotherapy or radiotherapy is performed prior to the increase of the level of the cells involved in immunity and the improvement of the function thereof. Low-dose chemotherapy is preferred, and step (1), (2), (3) and/or (4) are performed after the blood concentration of the chemotherapeutic agent for the chemotherapy reaches its peak value and falls down (namely, after the cytotoxic effect of the chemotherapeutic agent is diminished), so as to avoid the adverse effect of the chemotherapeutic agent on the immune system as much as possible during the application of the therapeutic method of the present invention. In the present invention, "the cells involved in immunity" include dedicated antigen-presenting cells and immune effector cells (for example, T cells).

The therapeutic method of the present invention can further comprise a step of administration of a molecular targeting agent for tumor to said tumor patient. The commonly used molecular targeting agents for tumor include monoclonal antibodies and small-molecule compounds which aim at specific targets on tumor cells. The main monoclonal antibodies and small-molecule compounds are listed in Table 1.

TABLE 1

Molecular targeting therapeutic agents for tumor

| Targets/Pathways | Agents |
| --- | --- |
| Estrogen receptor | Tamoxifen, Toremifene (Fareston ®), Anastrozole (Arimidex ®), exemestane (Aromasin ®), Letrozole (Femara ®) |
| BCR-ABL | Imatinibmesylate (Gleevec ®) |
| BRAF | Vemurafenib (Zelboraf ™) |
| CD20 | Rituximab (Rituxan ®), Ofatumumab (Arzerra ®), Tositumomab[131] I-tositumomab (Bexxar ®), Ibritumomabtiuxetan (Zevalin ®) |
| CD30 | Brentuximabvedotin (Adcetris ™) |
| CD52 | Alemtuzumab (Campath ®) |
| CTLA-4 | Ipilimumab (Yervoy ™) |
| EGFR | Gefitinib (Iressa ®), Erlotinib (Tarceva ®), Cetuximab (Erbitux ®), Panitumumab (Vectibix ®) |
| EML-ALK | Crizotinib (Xalkori ®) |
| Her2 | Trastuzumab (Herceptin ®), Lapatinib (Tykerb ®) |
| HDAC | Vorinostat (Zolinza ®), Romidepsin (Istodax ®) |
| IL-2 receptor | Denileukindiftitox (Ontak ®) |
| mTOR | Temsirolimus (Torisel ®), Everolimus (Afinitor ®) |
| Proteasomes | Bortezomib (Velcade ®) |
| RAR | Alitretinoin (Panretin ®), Tretinoin (Vesanoid ®) |
| RXR | Bexarotene (Targretin ®) |
| VEGFR | Bevacizumab (Avastin ®), Sorafenib (Nexavar ®), Sunitinib (Sutent ®), Pazopanib (Votrient ®) |
| Muti-target tyrosine kinase inhibitors | Dasatinib (Sprycel ®), Nilotinib (Tasigna ®), Vandetanib (Zactima ™) |

In a further preferred embodiment, nutrition support is given to the tumor patients during the whole treatment course, and the nutrition given by said nutrition support include proteins, fats, multivitamins, and trace elements.

In another aspect, the present invention provides a device for in vivo individualized systemic immunotherapy, comprising:
(1) a first unit, which is used for increasing release amount of tumor antigens at a tumor site where treatment is required in a tumor patient;
(2) a second unit, which is used for increasing level of proteins capable of adhering to and/or wrapping the tumor antigens;
(3) a third unit, which is used for increasing level of the dedicated antigen-presenting cells involved in immunity, and establishing, between the dedicated antigen-presenting cells and immune effector cells, a close connection capable of activating the immune effector cells at said tumor site;
(4) a fourth unit, which is used for increasing level of the immune effector cells and improving function thereof, thus establishing a close connection between the immune effector cells and target cells, resulting in killing of the target cells at said tumor site; and
(5) a fifth unit, which is used for making sure that the release amount of the tumor antigens, the level of the proteins capable of adhering to and/or wrapping the tumor antigens, the level of the dedicated antigen-presenting cells involved in immunity and the close connection between the dedicated antigen-presenting cells and the immune effector cells, and the level and function of the immune effector cells each reaches a maximum value at a respective time which overlaps with each other maximally, as well as at a respective site which overlaps with each other maximally.

In a further aspect, the present invention provides a method for optimizing the anti-tumor therapeutic method of the present invention (more specifically, making the maximum value of each of the steps (1)-(4) of the anti-tumor therapeutic method according to the present invention overlaps with each other maximally in time and space), comprising sequential steps of:

a) determining time ranges when the effect of each of the steps (1)-(4) reaches the maximum value, respectively;
b) assembling the steps (1)-(4) in an appropriate order and overlapping the time ranges to make sure the maximum effect of each of the steps (1)-(4) occurs simultaneously.

The present invention provides an anti-tumor therapeutic method with significantly improved efficacy compared to the prior art, and this therapeutic method targets individual tumor-specific antigen spectra and all the interactions occur in vivo, so it is an individualized, holographic, automatic and systemic immunotherapy. These properties are demonstrated through the following facts: First, the anti-tumor therapeutic method of the present invention involves almost all aspects of an immune response, namely, release of tumor-specific antigens, expression of the proteins capable of adhering to and/or wrapping the tumor antigens, presentation of the tumor antigens, the attack of the immune effector cells to tumor cells, and etc., so that not only can the tumor in situ (where the oncolytic agent is injected) be killed, but distal homologous tumor cells can also be self-identified and killed through activation of the immune system of human body, which will significantly improve the systemic therapeutic effect. Second, after the tumor-specific antigens are released from the tumor cells, they can be presented overall to the human immune system by proteins capable of adhering to and/or wrapping the tumor antigens, instead of being individually presented of some type of tumor-specific or tumor-associated antigens to the immune system, therefore, enhanced therapeutic effect can be achieved for individual patients. Third, the anti-tumor therapeutic method of the present invention takes into account the timing and site of occurrence of the following peak values: the level of released tumor antigens after lysis or killing of tumor cells; the expression level of the proteins capable of adhering to and/or wrapping the tumor antigens; the binding between the dedicated antigen-presenting cells and the immune effector cells, and the binding between the immune effector cells and the target cells, which are essential aspects in the immune responses; and the level of the cells involved in immunity and the function thereof. Thus, the immune response can be maximized by a synergistic effect achieved by overlapping all the above peak values in space and time as much as possible, and thereby the therapeutic effect is enhanced.

BRIEF DESCRIPTION OF THE DRAWINGS

Detailed description of the present invention will be explained by way of examples and with reference to the accompanying drawings.

FIG. 10A shows the comparison of the antitumor efficacy between the groups of H101, GM-CSF, PD-L1 mab, PD-L1 mab+GM-CSF, and PD-L1 mab+GM-CSF+H101; and FIG. 10B shows the comparison of the antitumor efficacy between the groups of GM-CSF, GM-CSF+H101, PD-L1 mab+GM-CSF, and PD-L1 mab+GM-CSF+H101.

FIG. 12A shows single administration of GM-CSF or PD-L1 mab induces medium $CD8^+$ TIL infiltration while non-assembling combinations (PD-L1 mab+(GM-CSF+H101)) and PD-L1 mab-GM-CSF-H101 groups) just induce low infiltration. FIG. 12B shows the density analysis data of FIG. 12A in green channel.

DETAILED DESCRIPTION OF THE INVENTION

Figure 1:
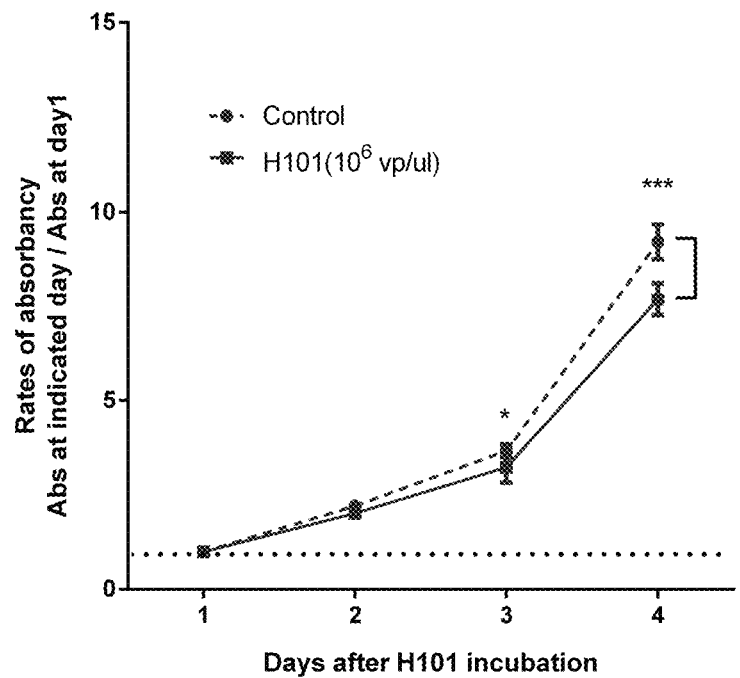
FIG. 1 shows evaluation of in vitro effect of H101 on murine B16 cell growth using CCK-8 kit, which indicates that treatment of H101 faintly represses B16 murine melanoma cells in vitro after 4 days; wherein the results were presented as mean±SEM; *$p<0.05$; ***$p<0.001$.

The anti-tumor therapeutic method provided in the present invention effectively combines oncolytic viral therapy and other therapies like immunotherapy, comprising the steps (in a non-sequential manner):

(1) Increasing release amount of tumor antigens at a tumor site where treatment is required in a tumor patient;

(2) at the tumor site, increasing level of proteins capable of adhering to and/or wrapping the tumor antigens;

(3) at the tumor site, increasing level of dedicated antigen-presenting cells involved in immunity, and establishing, between the dedicated antigen-presenting cells and immune effector cells, a close connection capable of activating the immune effector cells; and
(4) at the tumor site, increasing level of the immune effector cells and improving function thereof, thus establishing a close connection between the immune effector cells and target cells, resulting in killing of the target cells; and wherein the release amount of the tumor antigens in step (1), the level of the proteins capable of adhering to and/or wrapping the tumor antigens in step (2), the level of the dedicated antigen-presenting cells involved in immunity and the close connection between the dedicated antigen-presenting cells and the immune effector cells in step (3), and the level and function of the immune effector cells in step (4) each reaches a maximum value at a respective time which overlaps with each other maximally, as well as at a respective site which overlaps with each other maximally.

As used herein, the terms "maximum value" and "peak value" basically have the same meaning, and both refer to the value corresponding to the peak point of the wave demonstrating the change of certain substance's level or connection with time in each step.

The present invention effectively and synergistically combines oncolytic therapy and immunotherapy, and thus optimize the aspects in the anti-tumor immune response including release of tumor antigens, expression of proteins capable of adhering to and/or wrapping the tumor antigens, and improve the level and function of the cells involved in immunity; and it systematically and reasonably arranges the time and site of the occurrence of each of the above factors, so that they can function synergistically to the utmost extent, forming a specific cell-mediated immune response chain of the body against the tumor antigens having individual specificity, resulting in an optimal therapeutic effect.

In the practice, one or more of the following approaches can be used for increasing the release amount of tumor antigens at a tumor site where treatment is required:

Approach No. 1: An oncolytic agent is applied to the tumor site (by intratumor (i.t.) injection, for example). The oncolytic agent may be oncolytic microorganism. The said oncolytic microorganism may be oncolytic virus (OV) such as oncolytic adenovirus, oncolytic herpes simplex virus, oncolytic vesicular stomatitis virus, oncolytic newcastle disease virus, oncolytic poliovirus, oncolytic EB virus, and other oncolytic virus that can selectively replicate in tumor cells; it may also be oncolytic bacterium such as oncolytic *salmonella typhosa*, oncolytic *bifidobacterium*, oncolytic *Shigella*, oncolytic *Listeria*, oncolytic *bacillus pestis*, and other oncolytic bacterium that can selectively grow in tumor cells. The oncolytic agent can also be nucleic acid sequence which can encode pro-apoptotic gene, cytolytic gene, tumor necrosis factor gene, cysteine proteinase gene, γ-globulin gene, HA-1 antitrypsin gene, and other gene that plays a role in oncolysis.

Approach No. 2: Absolute ethyl alcohol, acetic acid, hot saline water, hot distilled water or other agents that can kill tumor cells is applied to said tumor site (by intratumor (i.t.) injection, for example).

Approach No. 3: Radiofrequency ablation, microwave coagulation, high intensive focused ultrasound, laserthermia, cryotherapy, or other treatment that can kill tumor cells is applied to said tumor site.

The administration doses of the approaches 1-3 can be effective amount for increasing the release amount of tumor antigens at a tumor site. For example, in the case of oncolytic virus, the administration doses thereof can be in the range of, for example, $5.0\times10^{11}$-$1.5\times10^{12}$vp (virus particles)/tumor site.

In the above step (2), the proteins capable of adhering to and/or wrapping the tumor antigens are preferably selected from MHC I, MHC II and heat shock protein. MHC II (major histocompatibility complex class II) molecules are a family of molecules normally found only on antigen-presenting cells such as dendritic cells, mononuclear phagocytes, some endothelial cells, thymic epithelial cells, and B cells, but may also be induced on other cells by interferon γ. The examples of the heat shock protein include HSP70, HSP30, HSP60, HSP90, HSP94, HSP96, HSP110 and other types of HSPs.

The level of MHC II can be increased by reagents that induce adoptive immune response, for example, antigens, target toxins or oncolytic virus (OV) such as oncolytic adenovirus H101.

As for the HSPs, stimulation can be applied to the patient for increasing the level of HSP at said tumor site; also, injection of oncolytic microorganism which can express massive number of HSP at the tumor site in step (1) can directly increase the level of HSP at the tumor site. The administration doses of such oncolytic microorganism can be effective amount for increasing the release amount of tumor antigens and the level of HSP at said tumor site.

Said stimulation can includes topical heat, hypoxia, chill, infection, radiation, alcohol and other type of stimulation which can induce cells to produce heat shock protein. Preferably, said topical heat includes application of topical heat to said tumor site such that the topical temperature is 1-7° C. higher than the patient's normal body temperature.

It is worth noting that although the steps included in this therapeutic method can be performed without following the order of the serial numbers of the steps, the preferred sequence is that the step for increasing the release of tumor antigens at a tumor site is performed prior to the step for increasing the level of proteins capable of adhering to and/or wrapping the tumor antigens.

In one embodiment of the present invention, the proteins capable of adhering to and/or wrapping the tumor antigens can be recognized by the dedicated antigen-presenting cells. An example of this kind of protein is said heat shock protein.

In one embodiment of the present invention, the proteins capable of adhering to and/or wrapping the tumor antigens are expressed on the dedicated antigen-presenting or tumor cells. An example of this kind of protein is said MHC II.

The step for increasing the level of the dedicated antigen-presenting cells including dendritic cells involved in immunity at said tumor site and the step for increasing the level of the immune effector cells including $CD8^+$ cytotoxic T cells and $CD4^+$ T helper cells and improving the function thereof at said tumor site can be achieved by administrating an immunotherapeutic agent to the tumor patient. The immunotherapeutic agent includes interleukin-2, interleukin-3, interleukin-12, granulocyte/macrophage colony-stimulating factor (GM-CSF), thymosin, tumor necrosis factor (TNF), interferon (INF), chemotactic factors, levamisole, immune co-stimulation molecules, and other molecules that can boost immune responses. The administration doses of the immunotherapeutic agents can be in the range of, for example, for rhGM-CSF, 3-10 µg/kg body weight.

The step for establishing, between the dedicated antigen-presenting cells and the immune effector cells, a close connection capable of activating the immune effector cells can be achieved through regulation of the function and expression of cytokines and chemokines which can inhibit or enhance the interaction between the dedicated antigen-presenting cells and the immune effector cells by administrating corresponding monoclonal antibodies or chemical compounds to the patient, which include Ipilimumab (MDX010) (Anti-CTLA4), Tremelimumab (Anti-CTLA4), BMS-663513 (Anti-CD137), BMS-936558 (Anti-PD1), CT-011 (Anti-PD1), MK-3475 (Anti-PD1), BMS-936559 (MDX-1105-01) (Anti-PDL1), TGN1412 (Anti-CD28), TRX518 (Anti-GITR), and other anti-OX40 and PD-L1 antibodies. The cytokines and chemokines which can enhance the interaction between dedicated antigen-presenting cells and the immune effector cells include TGF beta, IL1, IL6, IL-12, IL18; immune co-stimulation molecules, CD28, ICOS, 4-1BB, CD27, CD70, NKp30, CD137, GITR, and OX40. The cytokines and chemokines which can inhibit the interaction between the dedicated antigen-presenting cells and the immune effector cells include BTLA, KIR, LAG-3, TIM-3, A2aR, CTLA4, PD1 and PD-L1. The administration doses of the monoclonal antibodies and the chemical compounds can be in the range of, for example, for CTLA4 mab, 3-10 mg/kg body weight.

The step for establishing a close connection between the immune effector cells and the target cells, resulting in killing of the target cells, can also be achieved through regulation of the function and expression of cytokines and chemokines which can enhance or promote the binding between the immune effector cells and the target cells by administrating corresponding monoclonal antibodies or chemical compounds to the patient, which include Ipilimumab (MDX010) (Anti-CTLA4), Tremelimumab (Anti-CTLA4), BMS-663513 (Anti-CD137), BMS-936558 (Anti-PD1), CT-011 (Anti-PD1), MK-3475 (Anti-PD1), BMS-936559 (MDX-1105-01) (Anti-PDL1), TGN1412 (Anti-CD28), TRX518 (Anti-GITR), and other anti-OX40 and PD-L1 antibodies. The administration doses of the monoclonal antibodies and the chemical compounds can be in the range of, for example, 3-10 mg/kg body weight.

The administration of the immunotherapeutic agents, the monoclonal antibodies and chemical compounds to the patent can be performed through appropriate conventional matter for administrating them in the art, for example through subcutaneous (s.c.) injection, intratumor (i.t.) injection, intramuscular (i.m.) injection, intraperitoneal (i.p.) injection or intravenous (i.v.) injection.

It is preferably that the released amount of the tumor antigens (or the increased amount thereof) in step (1), the level of the proteins capable of adhering to and/or wrapping the tumor antigens (or the increased amount thereof) in step (2), the level of the dedicated antigen-presenting cells involved in immunity and the close connection between the dedicated antigen-presenting cells and immune effector cells (which determines the activation level of the immune effector cells) in step (3), and the level (or the increased amount thereof) and function (or the increase thereof) of the immune effector cells as well as the binding between the immune effector cells and the target cells (which determines the level of cytotoxicity) in step (4) each reaches a maximum value at a respective time which overlaps with each other maximally, as well as at a respective site which overlaps with each other maximally.

In the method according to the present invention, the following process can be used for making the maximum value of each step overlaps with each other maximally in time and space. That is, determining the time ranges when the effect of each step reaches the peak value, respectively; then assembling every step in an appropriate order and overlapping the time ranges to make sure the maximum effect of each step occurs substantially simultaneously.

In the method according to the present invention, the administration dose of each of agent is an effective amount for therapy.

In one preferred embodiment of the present invention, the anti-tumor therapeutic method comprising the steps of:
(i) applying oncolytic virus H101 to the tumor site for the step (1) and/or the step (2);
(ii) administrating GM-CSF to the tumor patient for the step (3);
(iii) administrating PD-L1 antibodies to the tumor patient for the step (4).

In the above embodiment, the administration dose of each of oncolytic virus H101, GM-CSF and PD-L1 antibody is an effective amount for therapy. For example, the dose of the oncolytic virus H101 is in the range of $5.0 \times 10^{11}$-$1.5 \times 10^{12}$ vp/tumor site; the dose of the GM-CSF is in the range of 3-10 µg/kg body weight; the dose of the PD-L1 antibody is in the range of 3-10 mg/kg body weight.

The administration of oncolytic virus H101, GM-CSF and PD-L1 antibody can be performed through appropriate conventional matter for administrating them in the art.

When a chemotherapeutic agent is applied, step (i), (ii), and/or (iii) are performed after the blood concentration of the chemotherapeutic agent reaches its peak value and falls down (namely, after the cytotoxic effect of the chemotherapeutic agent is diminished), so as to avoid the adverse effect of the chemotherapeutic agent on the immune system as much as possible during the application of the therapeutic method of the present invention.

Another aspect of the present invention also provides a device for in vivo individualized systemic immunotherapy, the device including the following units:
(1) a first unit, which is used for increasing the release amount of tumor antigens at a tumor site where treatment is required in a tumor patient;
(2) a second unit, which is used for increasing the level of proteins capable of adhering to and/or wrapping the tumor antigens at said tumor site;
(3) a third unit, which is used for increasing the level of the dedicated antigen-presenting cells involved in immunity, and establishing, between the dedicated antigen-presenting cells and the immune effector cells, a close connection capable of activating the immune effector cells at said tumor site;
(4) a fourth unit, which is used for increasing the level of the immune effector cells and improving the function thereof, thus establishing a close connection between the immune effector cells and the target cells, resulting in killing of the target cells at said tumor site;
(5) a fifth unit, which is used for making sure that the released amount of the tumor antigens, the level of the proteins capable of adhering to and/or wrapping the tumor antigens, the level of the dedicated antigen-presenting cells involved in immunity and the degree of the close connection between the dedicated antigen-presenting cells and the immune effector cells, and the level and function of the immune effector cells each reaches a maximum value at a respective time which overlaps with each other maximally, as well as at a respective site which overlaps with each other maximally.

The device may comprise a treatment part, a detection part, a control part, or the combination thereof.

The first unit may consist of: a part for application of an oncolytic agent at the tumor site; a part for application of absolute ethyl alcohol, acetic acid, hot saline water, hot distilled water, or other agent which can induce tumor cell death; a part for application of radiofrequency ablation, microwave coagulation, high intensive focused ultrasound, laserthermia, or cryotherapy; and/or a part for detection of the level of the released antigens; wherein, the part for detection of the level of the released antigens may detect the pattern and time-to-peak value regarding the release of the antigens by application of Western blot analysis for proteins such as Actin which act as internal controls. Furthermore, the detected value from the first unit may be transmitted to the fifth unit.

The second unit may consist of: a part for application of a stimulation to the patient for increasing the level of the proteins capable of adhering to and/or wrapping the tumor antigens (for example HSP) at said tumor site; a part for injection of oncolytic microorganism which can induce massive expression of said proteins (for example HSP); and/or a part for detection of the level of said proteins (for example HSP); wherein the part for detection of the level of said proteins (for example HSP) may detect the pattern and time-to-peak value regarding the release of said proteins (for example HSP) after topical heat stimulation by application of Western blot (WB) analysis for the corresponding antibodies to said proteins (for example HSP). Furthermore, the detected value from the second unit may be transmitted to the fifth unit.

The third unit may consist of: a part for application of monoclonal antibodies or chemical compounds, and immunotherapeutic agent, appropriate proteins and peptides; a part for detection of the level of dedicated antigen-presenting cells; and/or a part for detect the levels of cytokines and chemokines which can inhibit or enhance the interaction between the dedicated antigen-presenting cells and the immune effector cells; wherein the part for detection of the level of the dedicated antigen-presenting cells may function using a flow cytometry. Furthermore, the detected value from the third unit may be transmitted to the fifth unit.

The fourth unit may consist of: a part for application of the related monoclonal antibodies and chemical compounds, and immunotherapeutic agent, appropriate proteins and peptides; a part for detection of the level of the immune effector cells; and/or a part for detection of the cytokines and chemokines which can inhibit or enhance the interaction between the immune effector cells and the target cells; wherein the part for detection of the level of the immune effector cells may function using a flow cytometry. Furthermore, the detected value from the fourth unit may be transmitted to the fifth unit.

The fifth unit is used for receiving and analyzing the values from the first, second, third, and fourth units and thereby controlling and regulating the operation of the first, second, third, and fourth units, so as to make sure that the released amount of the tumor antigens, the level of the proteins capable of adhering to and/or wrapping the tumor antigens, the level of the dedicated antigen-presenting cells involved in immunity and the close connection between the dedicated antigen-presenting cells and immune effector cells, and the level and function of the immune effector cells each reaches a maximum value at a respective time which overlaps with each other maximally, as well as at a respective site which overlaps with each other maximally.

The initiation of the operation of the first, second, third, and fourth units may be or may not be triggered by the fifth unit.

In a further preferred embodiment, oncolytic therapy, immunotherapy and nutrition support can be combined to provide a further preferred therapy, called CHINA therapy; wherein, C stands for "Cancer antigen release", that is, the release of cancer antigens; H stands for "HSP increase", that is, the increase of the level of HSP; I stands for "Immunostream formation", that is, formation of an immune stream; N stands for "Nutrition support"; A stands for "Assembly" which refers to an effective and synergistic combination of all the factors and particularly means herein that the maximum value of each step overlaps with each other maximally in time and space.

The mechanism of action of CHINA therapy is described hereunder, wherein an oncolytic agent and topical heat stimulation are used as an example. The oncolytic agent can kill tumor cells, and at the same time, will induce the release of various tumor antigens having individual specificity, and application of topical heat to the tumor site where the oncolytic agent is injected can induce the production of "inducible HSPs". These HSPs will bind to various tumor antigens released after lysis of the tumor cells, and also will bind to the specific receptors (CD91) on the surface of dendritic cells, so as to present the antigens to immature dendritic cells. The HSP70 produced by application of heat can also significantly speed up the maturation process of dendritic cells. Dendritic cells are the most potent dedicated antigen-presenting cells in human body, and they will process antigens during their maturation, and they possess migration ability and will migrate to the lymphoid organs of human body, and then, the MHC II molecules on DC surface will present the processed tumor antigens to $CD4^+$ T cells, and the MHC I molecules on DC surface will present the processed tumor antigens to $CD8^+$ T cells, which will stimulate a specific immune response against the tumor cells, resulting in systemic and long-lasting induction of tumor cell death through immune effector cells. From the above description, it can be concluded that CHINA therapy can effectively and synergistically combine oncolytic therapy and immunotherapy, and thus optimize the aspects in the anti-tumor immune response including release of tumor antigens, expression of HSPs and maturation of DCs, and improve the function of the cells involved in immunity; and it systematically and reasonably arranges the time and site of the occurrence of each of the factors, so that they can function synergistically to the utmost extent, forming a specific cell-mediated immune response chain of the body against the tumor antigens having individual specificity, resulting in an optimal therapeutic effect.

Surely, in the practice, the anti-tumor therapeutic method of the present invention may also consist of, low-dose chemotherapy for example, radiotherapy or molecular targeted therapy for tumor. It's preferred that chemotherapy or radiotherapy is performed prior to the increase of the amount of cells involved in immunity. At present, the commonly employed molecular targeting therapeutic agents for tumor including monoclonal antibodies and small-molecule compounds can be used in this therapeutic method of the present invention (the examples thereof are listed in Table 1).

The following embodiment using oncoytic adenovirus H101 is described in detail to demonstrate the anti-tumor therapeutic method of the present invention.

The present embodiment comprises the following steps:

1. Deciding the tumor site where treatment is required, and apply low-dose chemotherapy and/or radiotherapy to it;

2. Injecting the oncolytic adenovirus H101 into said tumor site where treatment is required, so as to specifically kill the tumor cells and induce the release of tumor antigens;

3. Applying heat to said tumor site where treatment is required until the temperature of the site where heat was applied is 1-7° C. higher than the patient's normal body temperature, so as to locally induce the expression of HSPs;

the HSPs will carry the released tumor antigens and present them to dedicated antigen-presenting cells, which will stimulate the immune response against the tumor cells in vivo, therefore, both local and metastatic tumors will be affected;

4. Inducing immune regulation during the course of treatment. Immune regulation may be promoted through application of immunotherapeutic agents. The immunotherapeutic agents can be IL-2, IL-3, IL-12, GM-CSF, thymosin, TNF, INF, chemotactic factors, levamisole, immune co-stimulation molecules, and other molecules that can boost immune responses. GM-CSF can bind to the specific receptors on the surface of the precursor cells of granulocytes and mononuclear macrophages, stimulating the proliferation of these precursor cells and the differentiation of them into neutrophile granulocytes, eosinophile granulocytes and mononuclear macrophages; IL-2 can stimulate the proliferation of cytotoxic T cells, natural killer cells and lymphokine-activated killer cells, and enhance the killing activities thereof, and it will also stimulate the production of antibodies and Interferons by lymphocytes, thus participate in the regulation of anti-tumor immune responses; Thymosin is used to induce the differentiation of T cells into mature T cells, stimulate the production of cytokines, and enhance the antibody-mediated immune response of B cells; and 5. Providing the patient with nutrition support throughout the course of treatment, which includes the supplements of amino acids, fats and trace elements for nutritional balance.

During the above treatment course, the level of released tumor antigens reaches its peak value at 2-7 days after intratumoral injection of oncolytic adenovirus; the expression of HSPs reaches its peak value at 2-6 hours after topical heat application; the effect of GM-CSF reaches its peak value at about 7 days after administration; the effects of IL-2 and thymosin reach their peak values at around 5 days after administration. The optimal therapeutic effect of the systemic immunotherapy will be achieved when all the above peak values from application of the aforementioned therapeutic agents and treatments overlap spatially and temporally. The person skilled in the art should appreciate that it is easy to adjust the peak value of the expression of HSPs to be overlap with other peak values as the expression of HSPs merely needs 2-6 hours after topical heat application to reach peak value.

It needs to be noted that in the above embodiment, oncolytic microorganism is not limited to oncoytic adenovirus H101, and the oncolytic microorganisms disclosed in the Chinese patent application publication No. CN1412295A with the title "Oncolytic microorganisms expressing heat shock proteins and their applications" may also be used, provided that the aforementioned steps will be adjusted according to the feature of each oncolytic microorganism. For example, when oncolytic adenovirus H103 which can express HSPs is employed, the aforementioned application of topical heat in step 3 can be skipped and the HSPs expressed by H103 will play a role in stimulation of immune responses.

In the following example, non-small cell lung cancer is treated.

Figure 18:
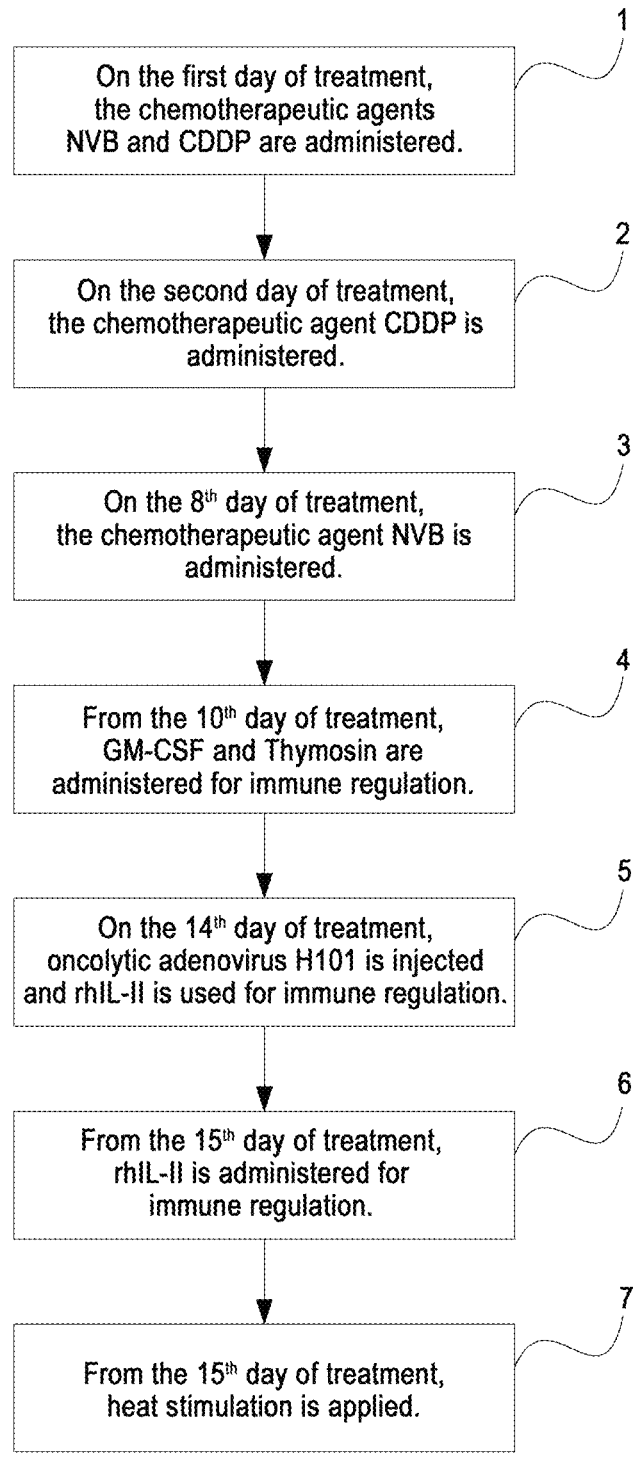
FIG. 18 shows a flowchart of an embodiment of an anti-tumor therapeutic method.
Figure 19:
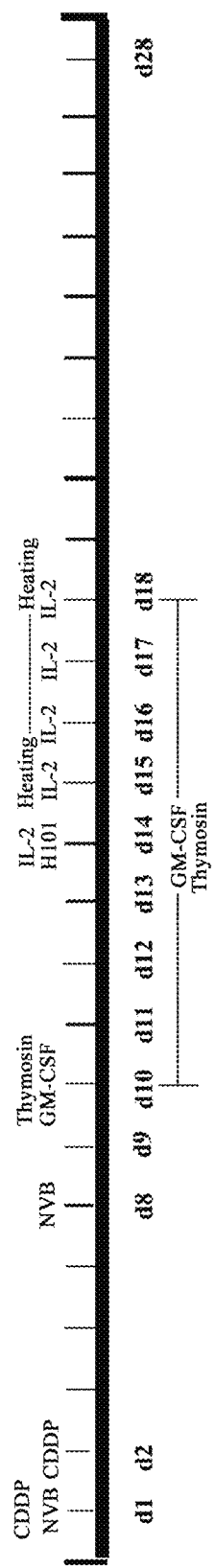
FIG. 19 shows a schematic representation of a drug administration schedule for one course of treatment in the embodiment shown in FIG. 18.

Please also refer to FIG. 18 and FIG. 19, simultaneously. First, the duration of a course of treatment is fixed to be 28 days. In this embodiment, the anti-tumor therapeutic method comprises the steps of:

1. On the first day of treatment: first, Vinorelbine (NVB) 25 mg/m$^2$ is diluted in 100 ml of normal saline and administered through intravenous infusion for 15-30 minutes; and then 250 ml of normal saline is injected fast to irrigate the vein, and cisplatin (CDDP) 40 mg/m$^2$ is given through intravenous infusion with hydration.

2. On the second day of treatment: Cisplatin (CDDP) 40 mg/m$^2$ is administered through intravenous infusion with hydration.

3. On the 8th day of treatment: first, Vinorelbine (NVB) 25 mg/m$^2$ is diluted in 100 ml of normal saline and administered through intravenous infusion for 15-30 minutes; and then 250 ml of normal saline is injected fast to irrigate the vein.

4. On the 10th, 12th, 14th, 16th, and 18th day (once every other day): subcutaneous injection of GM-CSF 150 ug, qd; on the 10th, 12th, 14th, 16th, and 18th day (once every other day): subcutaneous injection of thymosin α1 1.6 mg.

5. On the day 14: intratumor injection of 5 vials of H101 ($5 \times 10^{11}$ VP/vial)+1,000,000 units of rhIL-2.

6. On the day 15 to 18 (4 consecutive days): intramuscular injection of 1,000,000 units of rhIL-2, qd.

7. On the day 15 to 18 (4 consecutive days): application of radio frequency heating (42.5° C.) to the chest area for one hour, qd.

Wherein, intra-tumor injection of IL-2 is for improving the "microenvironment" within the tumor where IL-10 and TGF-β (transforming growth factor-β) are dominant and facilitate the growth of the tumor cells; the application of GM-CSF may boost the maturation of DCs; the application of thymosin is for improving the effect of T cells.

In FIG. 19, d1 refers to the first day, d2 refers to the second day, and so on.

In this embodiment, application of radio frequency heating (42.5° C.) to the chest area for 4 consecutive days from day 15 to 18 of treatment will induce the expression of HSP at the chest area, therefore, the site where tumor antigens are released and the site where endogenous HSP are expressed through application of topical heat are the same, so that spatial overlap of these two factors for the immune response can be achieved, resulting in an improved therapeutic effect. Hereinafter, the present invention will be described in more details by way of examples with reference to the figures. The objects, features, and aspects of the present invention are disclosed in or are apparent from the following description. It is to be understood by one of ordinary skill in the art that the description is provided for the purpose of illustrating exemplary embodiments only, and is not intended to limit broader aspects of the present invention, which broader aspects are embodied in the exemplary constructions.

Materials and Methods

Cell Viability Assay (for FIG. 1)

The effect of H101 on murine B16 cell growth in vitro was assessed by CCK-8 kit. B16/F0 murine melanoma cells (i.e., B16 cells) were purchased from Shanghai Cell Bank, Type Culture Collection Committee, Chinese Academy of Sciences. The cells were cultured in DMEM medium supplemented with 10% (v/v) heat inactivated FBS, 100 U/ml penicillin, 100 μg/ml streptomycin (herein after referred to as "culture medium") and maintained at 37° C. in a humidified atmosphere of 5% $CO_2$. Oncolytic virus (OV) H101 (Brand name: Oncorine; $5 \times 10^{11}$VP/0.5 mL/ampoule) was purchased from Shanghai Sunway Biotech. Briefly, the B16 cells were dispensed into 96 wells plates at $0.5 \times 10^4$/200 μL culture medium per well, respectively. The B16 tumor cells were then treated with H101 at indicated virus particles (VP) or 50 μl PBS (pH 7.4) without H101 (control group) and cultured for the indicated time periods. At different time points (post 1, 2, 3, 4 days) after infection, the proliferation of cells was analyzed using CCK-8 kit (Dojindo Laboratories, Kumamoto, Japan) according to manufacturer's protocols.

Figure 2:
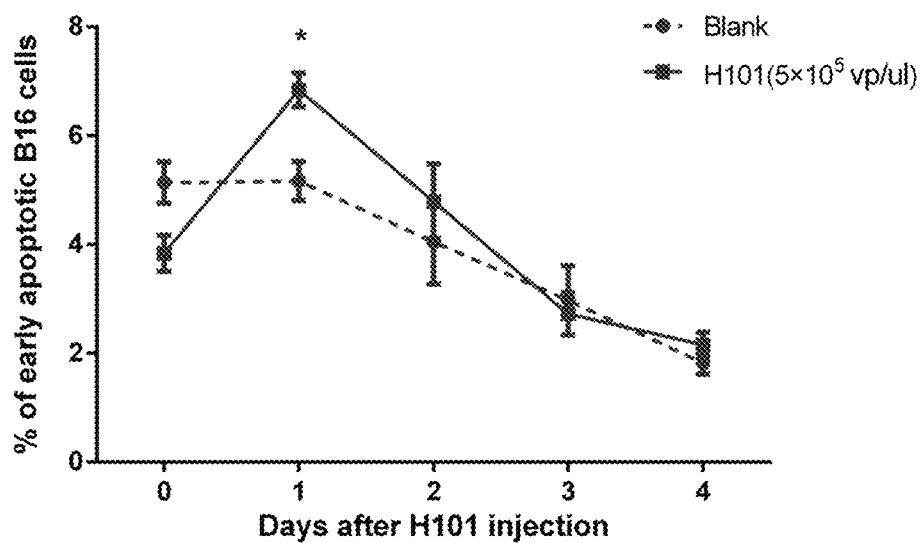
FIG. 2 shows evaluation of apoptosis effects of H101 on B16 cells using Annexin V-FITC and PI double staining by flow cytometry (Annexin $V^+$ $PI^-$), which indicates that treatment of H101 to B16 cells induces early stage of apoptosis post 24 h in vitro; wherein the results were presented as mean±SEM; *$p<0.05$.
Figure 3:
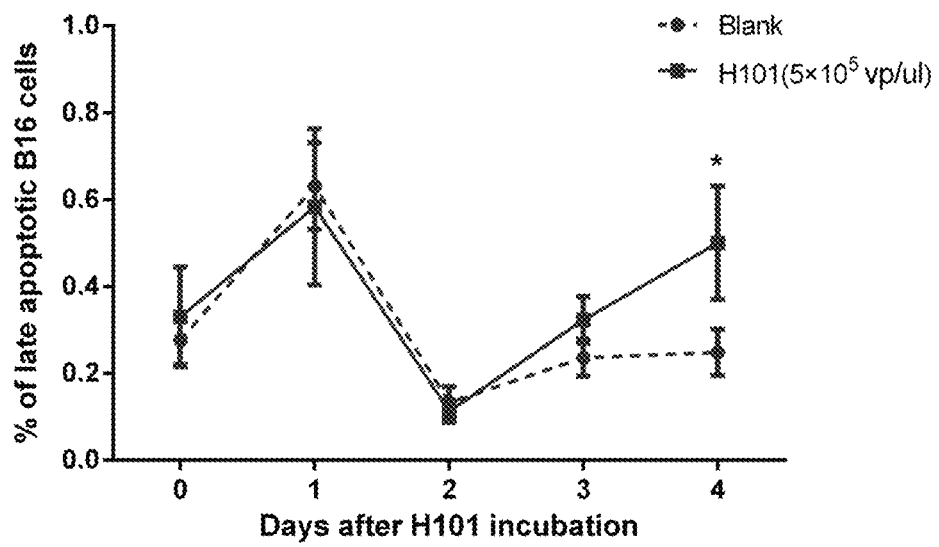
FIG. 3 shows evaluation of necrosis effects of H101 on B16 cells using Annexin V-FITC and PI double staining by flow cytometry (Annexin V+PIP), which indicates that treatment of H101 to B16 cells induces late stage of apoptosis (necrosis) post 3-4 days in vitro; wherein the results were presented as mean±SEM; *$p<0.05$.

Flow Cytometric Analysis of Apoptosis and Necrosis (for FIGS. 2 and 3)

The apoptosis and necrosis effects of H101 on B16 cells were analyzed using Annexin V-FITC and PI double staining by flow cytometry. The Annexin V-FITC and PI assay kit (Annexin V-FITC Apoptosis Detection Kit 300 test, BMS500FI/300) were purchased from eBioscience. Briefly, the B16 murine tumor cells ($1\times10^6$) were treated with H101 at indicated concentration or 50 μl PBS (pH 7.4) without H101 (Blank) in culture medium for indicated times. The untreated and H101-treated cells were harvested, washed, resuspended in 1× Annexin V binding buffer (provided by the assay kit) ($1\times10^5$ cells/100 μL) and incubated with Annexin V-FITC and PI (stock solution provided by the assay kit, 5 μL each). After 15 min of incubation at room temperature (RT), the cells were then analyzed by flow cytometry (BD Accuri™ C6 flow cytometer).

Figure 4:
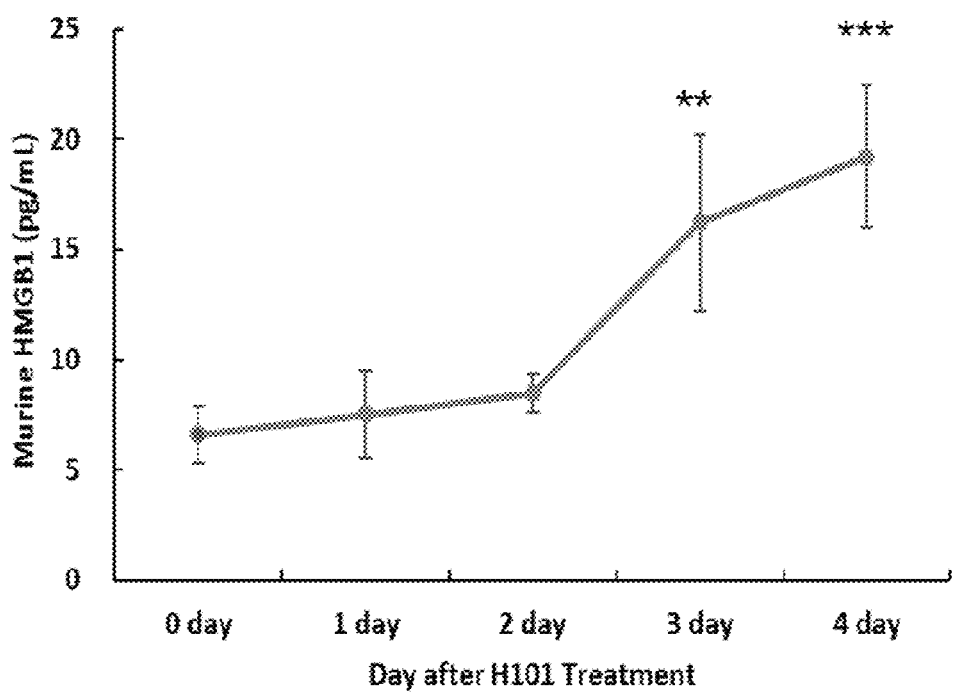
FIG. 4 shows evaluation of oncolytic effect of H101 on B16 cell line in vitro by measuring release of murine HMGB1 protein in cell culture supernatant using ELISA method, which indicates that treatment of H101 to B16 cells causes the release of HMGB1 protein post 3-4 days in vitro; wherein the results were presented as mean±SEM; $p<0.01$; *$p<0.001$.

Murine HMGB1 ELISA Assay (for FIG. 4)

To estimate the oncolytic effect of H101 on B16 cell line in vitro, release of murine HMGB1 protein was measured in cell culture supernatant using ELISA method. The murine HMGB1 protein ELISA kit was purchased from Antibodies-online (Cat# ABIN415379). Briefly, the B16 murine tumor cells ($1\times10^6$) were treated with H101 at $5\times10^8$ VP/mL in culture medium for indicated times. The cell culture of untreated and H101-treated cells were harvested, centrifuged, and then, the obtained supernatants were analyzed using murine HGMB1 protein ELISA kit according to manufacturer's protocols.

Animal Model (for FIGS. 5-11)

The male immunocompetent C57BL/6 mice were purchased from Shanghai Experimental Animal Center (Shanghhai, China) and maintained in the animal facility at Tongji University (Shanghai, China) according to the animal research committee's guidelines of Tongji University. To establish the tumor-bearing animal model, the male immunocompetent C57BL/6 mice 6-8 weeks old, were subcutaneously (s.c.) inoculated on their back of the ribs with $2\times10^6$ B16 cells, and then monitored daily for tumor growth. After 6 days (when the tumors grew up to a mean tumor volume of around 70-100 mm³), these tumor-bearing animals were randomly numbered and then divided into groups depended on the random number. Tumor volume was measured with a caliper each three days and calculated using the following formula: $[L\times W^2]/2$ (L=length of tumor; W=width of tumor). On indicated days, mice were sacrificed by cervical dislocation; serum/plasma was collected and saved; spleen and the tumors were collected and weighed. Part of tumor was fixed by 4% (v/v) Paraformaldehyde and embedded in paraffin for immunofluorescence analysis. Part of tumor and entire spleens were dissociated, and then flow cytometric analysis was performed according to different purposes.

Figure 5:
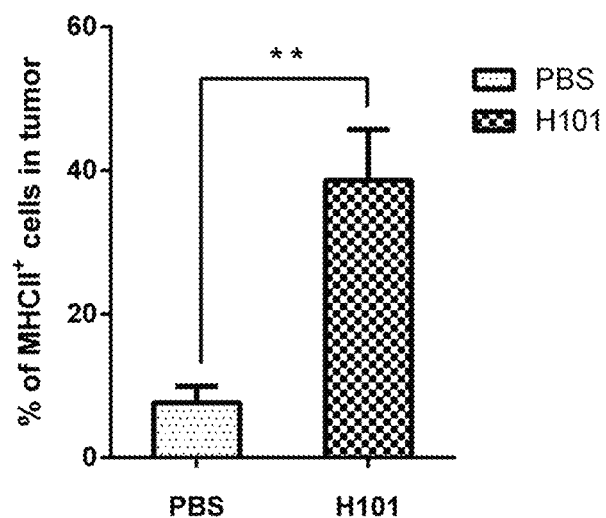
FIG. 5 shows evaluation of effect of H101 on the expression of MHCII at tumor site of tumor-bearing mice by flow cytometry, which indicates that administration of H101 i.t. in vivo induces high expression of MHCII at tumor site; wherein the results were presented as mean±SEM; **$p<0.01$.

Tumor Tissue Dissociation (for FIG. 5)

To maximize cell yield and viability, collagenase I and IV (200 U/ml; Sigma-Aldrich, St Louis, Mo., USA) were used. Briefly, mice were killed, and tumors were removed into cold culture medium and processed immediately. Surrounding mouse tissue and fat were removed. The tumors were minced into 2-3 mm fragments, which were then incubated with the dissociation solutions (containing collagenase I and IV, each 200 U/ml in cold PBS (pH 7.4)), for 30 min at 37° C. The tumor fragments were mixed up and down every 10 min using a 1.5 mL micropipette with a tip cut to a diameter adapted to tissue fragment size. After each incubation period, the fragments were filtered through a 40 mm nylon mesh cell strainer (BD Biosciences, San Diego, Calif., USA). The released cells were centrifuged at 1200 RPM for 2 min and stored in cold culture medium with 30% (v/v) FCS at 4° C. Fresh dissociation solution was added to the remaining tissue fragments for 30 min. Dissociation was stopped when no additional cells were released. The fragments were pushed through a sieve and all cells from all incubation periods were pooled and counted.

Figure 6:
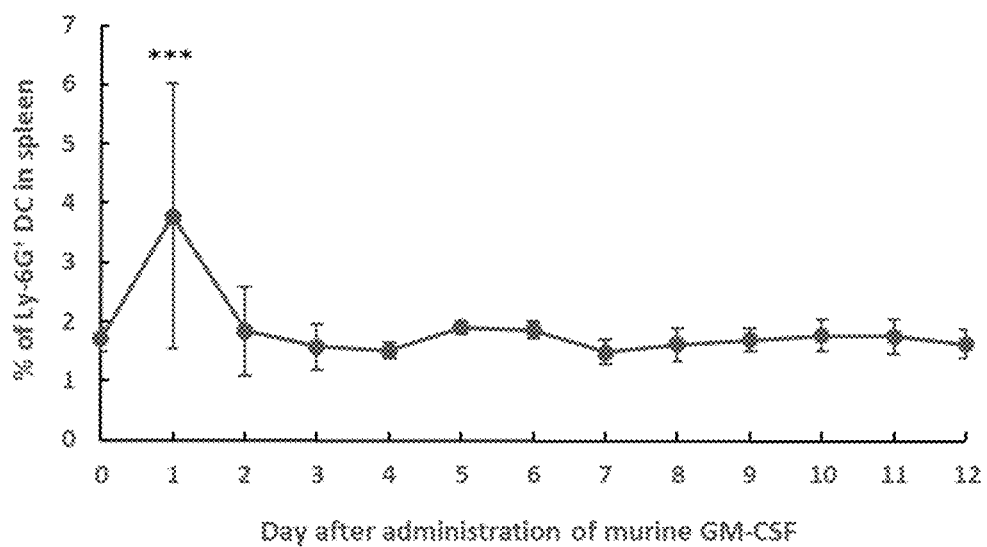
FIG. 6 shows evaluation of effect of GM-CSF on Ly-$6G^+$ DC precursor set in spleen of healthy mice by flow cytometry, which indicates that administration of murine GM-CSF s.c. induces expansion of Ly-$6G^+$ DC precursors at day 1 post injection in spleen of healthy C57BL/6 mice; wherein the results were presented as mean±SEM; ***$p<0.001$.
Figure 7:
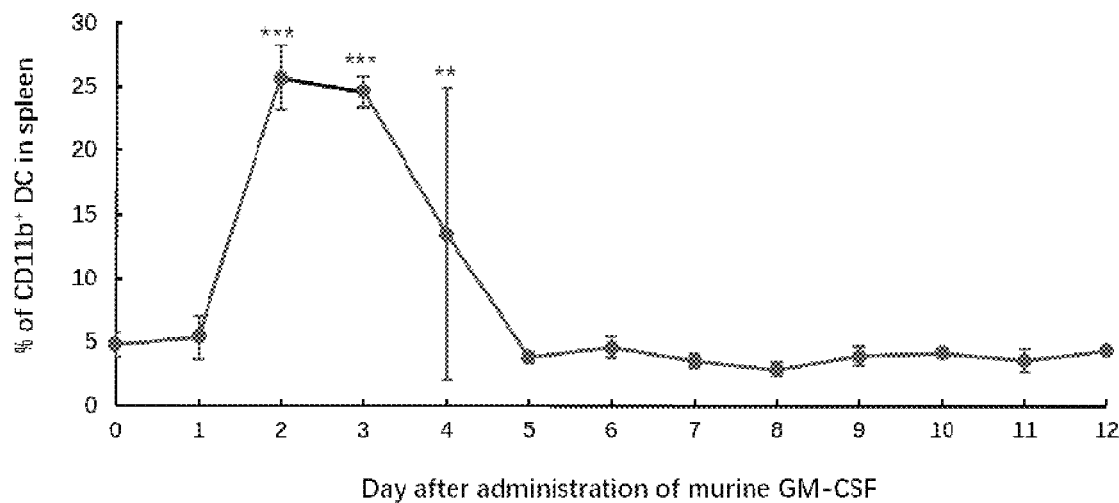
FIG. 7 shows evaluation of effect of GM-CSF on $CD11b^+$ DC set in spleen of healthy mice by flow cytometry, which indicates that administration of murine GM-CSF s.c. induces expansion of $CD11b^+$ DC at day 2-4 post injection in spleen of healthy C57BL/6 mice; wherein the results were presented as mean±SEM; $p<0.01$; *$p<0.001$.
Figure 8:
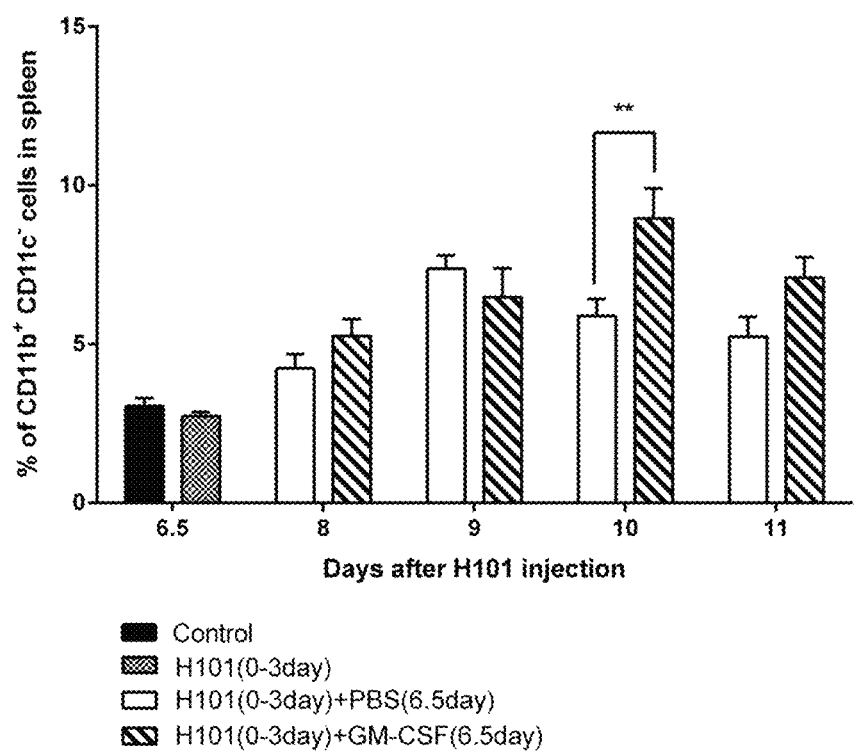
FIG. 8 shows evaluation of effect of GM-CSF on $CD11b^+$ DC set in spleen of tumor-bearing mice by flow cytometry, which indicates that administration of murine GM-CSF s.c. in B16 melanoma cell murine model induces up-regulation of $CD11b^+$ DC in spleen at Day 3.5 post injection; wherein the results were presented as mean±SEM; **$p<0.01$.

Spleen Tissue Dissociation (for FIG. 6-8)

Briefly, mice were killed, and spleens were removed into cold culture medium and processed immediately. Surrounding mouse tissue and fat were removed. The spleens were minced into 2-3 mm fragments, and then crushed in cold culture medium using a flat tail of syringe piston. The spleen fragments were mixed up and down several times using a 1.5 mL micropipette with a tip cut to a diameter adapted to tissue fragment size. After that, the fragments were filtered through a 40 mm nylon mesh cell strainer (BD Biosciences, San Diego, Calif., USA). The released cells were centrifuged at 1200 RPM for 2 min and stored in cold culture medium with 30% (v/v) FCS at 4° C. All cells from all incubation periods were pooled and counted.

Flow Cytometric Analysis of MHCII Expression on Tumor Site In Vivo (for FIG. 5)

Figure 13:
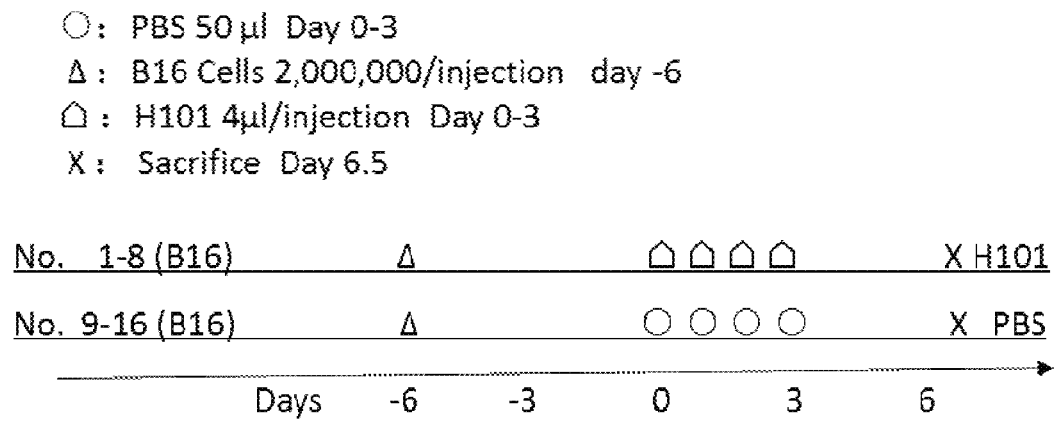
FIG. 13 is a flowchart showing the grouping and experiment design for flow cytometric analysis of MHCII expression on tumor site in vivo in Experimental example 2 of the present application.

16 male 6-8 weeks old C57BL/6 mice, were subcutaneously (s.c.) inoculated on their back of the ribs with $2\times10^6$ B16 cells. After 6 days, these tumor-bearing animals were randomly subjected to OVs therapy by multi-point intratumoral (i.t.) injection of H101 ($4\times10^9$ VPs) or PBS (pH 7.4, 50 μl) daily for a total 4 times (6 mice each group). The tumor-bearing mice were sacrificed after another 3.5 days. Tumors were dissociated, and then staining with PE-anti mouse I-A/I-E antibody (0.5 μg/40 μl) (eBioscience, Cat#12-5322-81). After washing, flow cytometric analysis (using BD Accuri™ C6 flow cytometer) was performed. Grouping and experiment design are illustrated in FIG. 13.

Flow Cytometric Analysis of GM-CSF Induced Expansion of DC and DC Precursorin Normal Animals (for FIG. 6, 7)

Figure 14:
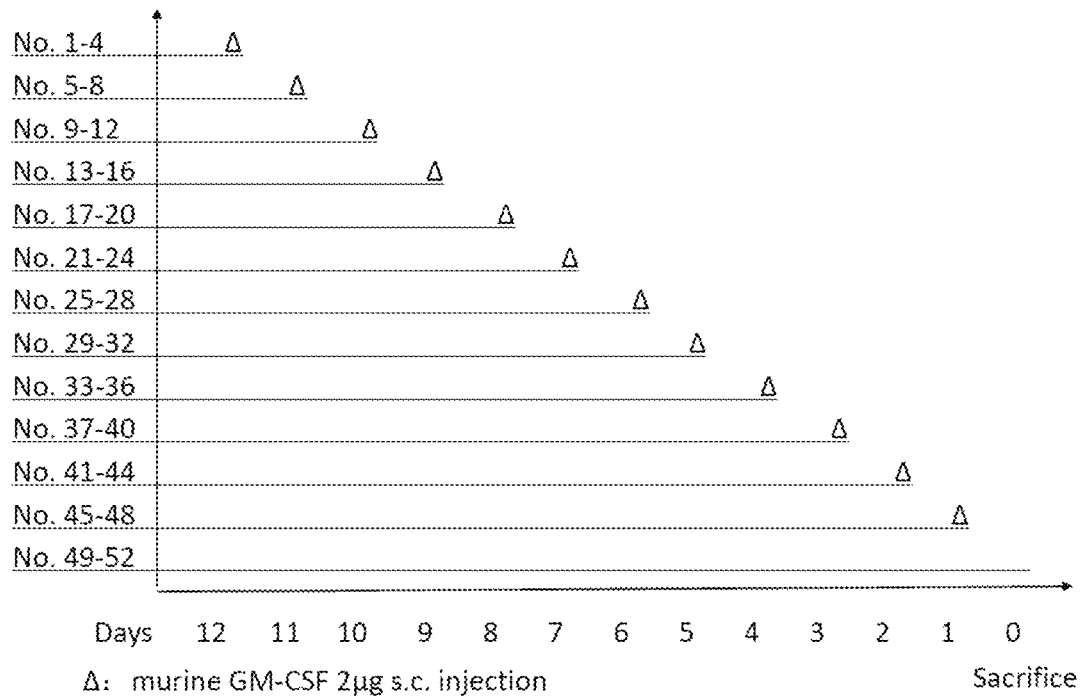
FIG. 14 is a flowchart showing the grouping and experiment design for flow cytometric analysis of GM-CSF induced expansion of DC and DC precursor in normal animals in the Experimental example 3 of the present application.

52 male 6-8 weeks old C57BL/6 mice were randomly numbered and then divided into 13 groups depended on the random number. 12 groups were subcutaneously (s.c.) administered murine GM-CSF (PeproTech, Cat#96-315-03-1000) 2 μg on their back of the ribs, single injection from day 1 to 12 respectively. The last group was control. After 13 days, all animals were sacrificed. Spleens of these animals were collected and dissociated, and then stained with anti-mouse FITC-CD11b (0.5 μg/40 μl) (BD Pharmingen, Cat#553310) and PE-Ly-6G (0.5 μg/40 μl) (BD Pharmingen, Cat#551461) antibodies. After washing, flow cytometric analysis (using BD Accuri™ C6 flow cytometer) was performed. Grouping and experiment design are illustrated in FIG. 14.

Flow Cytometric Analysis of GM-CSF Induced Expansion of DC in B16 Melanoma Cell Murine Model (for FIG. 8)

Figure 15:
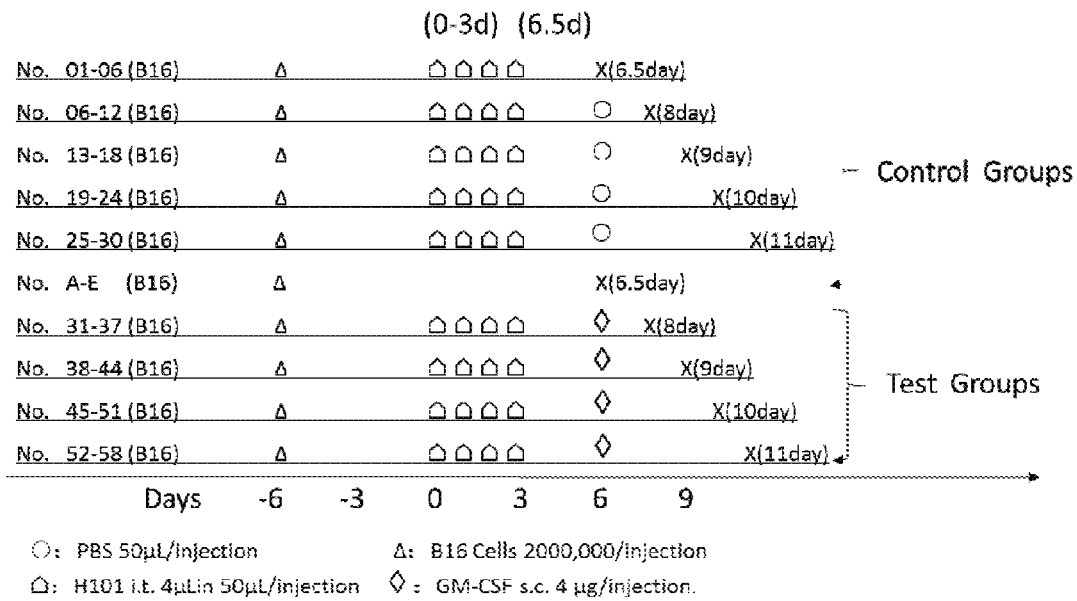
FIG. 15 is a flowchart showing the grouping and experiment design for flow cytometric analysis of GM-CSF induced expansion of DC in B16 melanoma cell murine model in the Experimental example 3 of the present application.

63 male 6-8 weeks old C57BL/6 mice were subcutaneously (s.c.) inoculated on their back of the ribs with $2\times10^6$ B16 cells, and then monitored daily for tumor growth. After 6 days (when the tumors grew up to a mean tumor volume of around 70-100 mm³), these tumor-bearing animals were randomly numbered and then divided into 10 groups depended on the random number. All animals were subjected to OVs therapy by multi-point intratumoral (i.t.) injection of H101 ($4\times10^9$ VPs) daily for a total 4 times except the control mice. After another 3.5 days, indicated groups were sacrificed and analyzed with FITC-CD11b (0.5 μg/40 μl) (BD Pharmingen, Cat#553310) and PE-CD11c (0.5 µg/40 µl) (BD Pharmingen, Cat#553802) antibodies, respectively; 4 groups were administrated subcutaneously with murine GM-CSF (PeproTech, Cat#96-315-03-1000) 4 µg on their back of the ribs, single injection; 4 groups were administrated subcutaneously with PBS (pH 7.4, 50 µL) on their back of the ribs, single injection. After another 1.5, 2.5, 3.5 and 4.5 days, indicated groups were sacrificed and analyzed, respectively. Grouping and experiment design are illustrated in FIG. 15.

Figure 9:
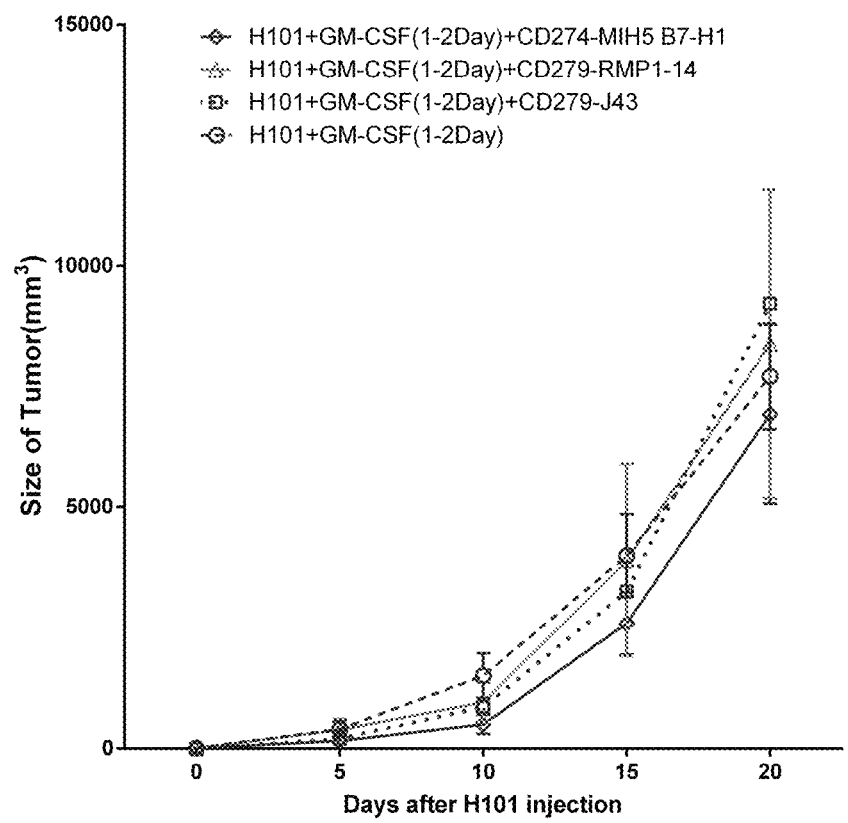
FIG. 9 shows evaluation of effect of immune checkpoint inhibitors on tumor growth of tumor-bearing mice, which indicates that administration of murine PD-L1 mab i.p. in B16 melanoma murine model represses tumor growth, better than that of PD-1 mabs; wherein the results were presented as mean±SEM.

Administration of Murine PD-L1 Antibodies In Vivo (for FIG. 9)

Figure 16:
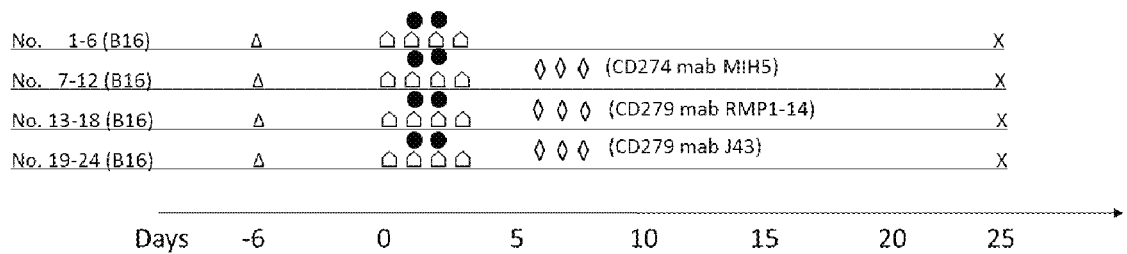
FIG. 16 is a flowchart showing the grouping and experiment design for administration of murine PD-L1 antibodies in vivo in the Experimental example 4 of the present application.

24 male 6-8 weeks old C57BL/6 mice were subcutaneously (s.c.) inoculated on their back of the ribs with $2 \times 10^6$ B16 cells, and then monitored daily for tumor growth. After 6 days (when the tumors grew up to a mean tumor volume of around 70-100 mm$^3$), these tumor-bearing animals were randomly numbered and then divided into 4 groups depended on the random number. All animals were subjected to OVs therapy by multi-point intratumoral (i.t.) injection of H101 ($4 \times 10^9$ VPs) daily for a total 4 times. After another 3 days, indicated groups were administrated murine immune checkpoint antibodies (i.e., CD274 mab MIH5, CD279 mab RMP1-14 and CD279 mab J43) (eBioscience, Cat#16-5982-85; 16-9982-85 and 16-9985-85, respectively) 125 µg each time on their back of the ribs, i.t. After another 17 days, all animals were sacrificed. All animals were administrated subcutaneously with murine GM-CSF (PeproTech, Cat#96-315-03-1000) 2 µg daily for a total 2 times on their back of the ribs at indicated times. Grouping and experiment design are illustrated in FIG. 16.

Figure 10A:
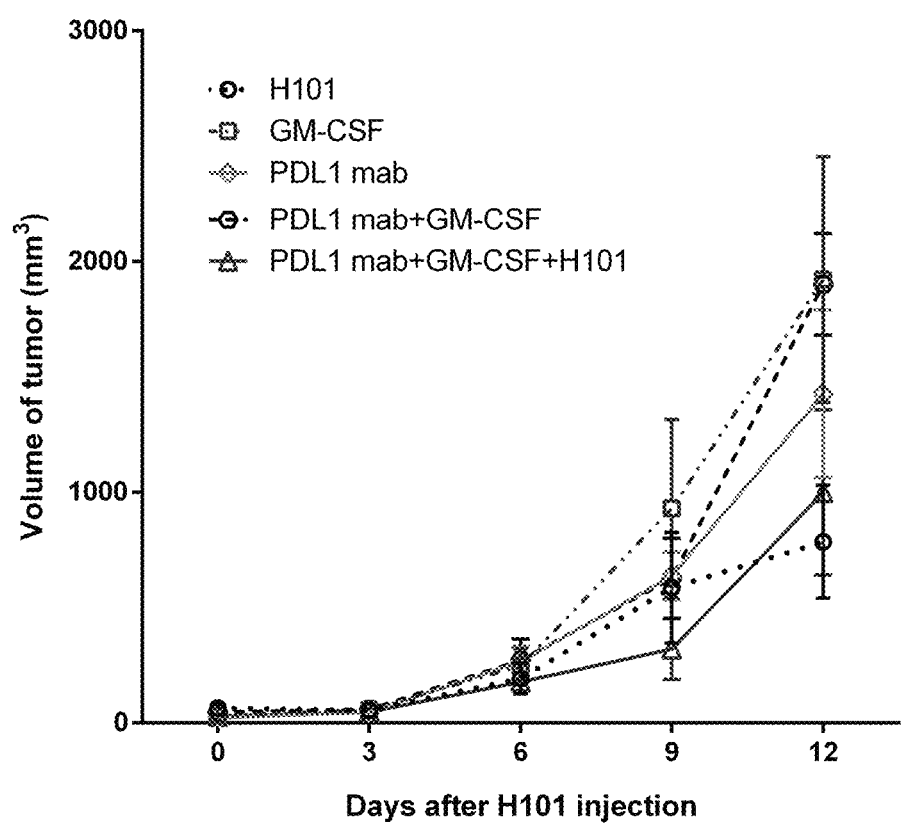
FIGS. 10A and 10B show comparison of effect of the systemic assembling group and non-systemic assembling groups on tumor growth of tumor-bearing mice, which indicates that comparing to single reagent or double reagents, the triple reagents (PD-L1 mab+GM-CSF+H101) exhibited the best antitumor efficacy; wherein the results were presented as mean±SEM. Specifically.
Figure 10B:
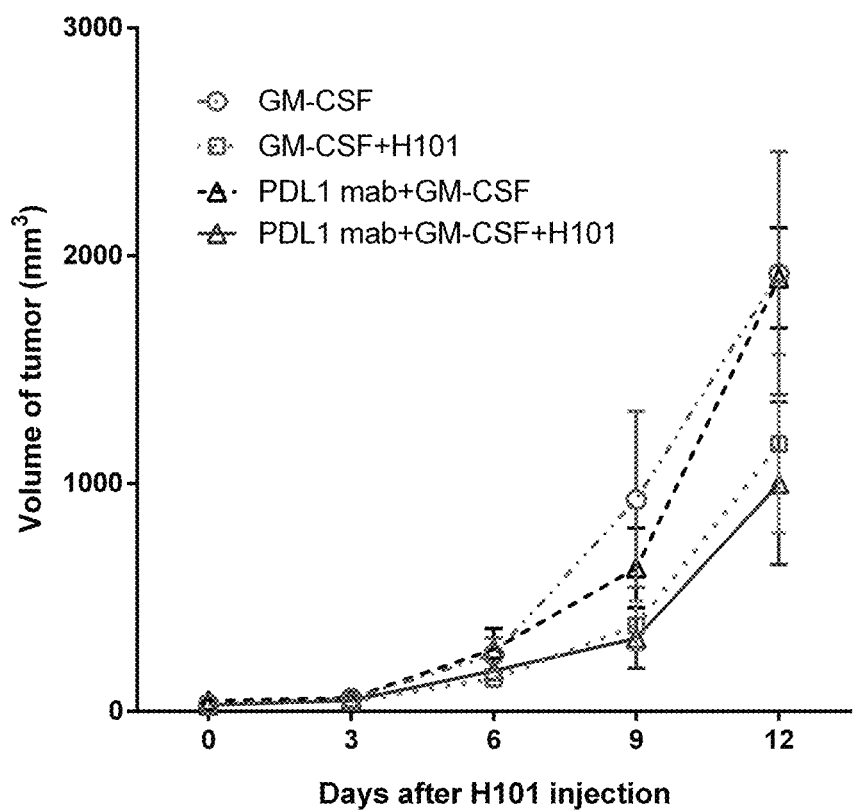

Systemic Immunotherapeutic Combination Therapy (for FIG. 10, 11, 12)

Figure 17:
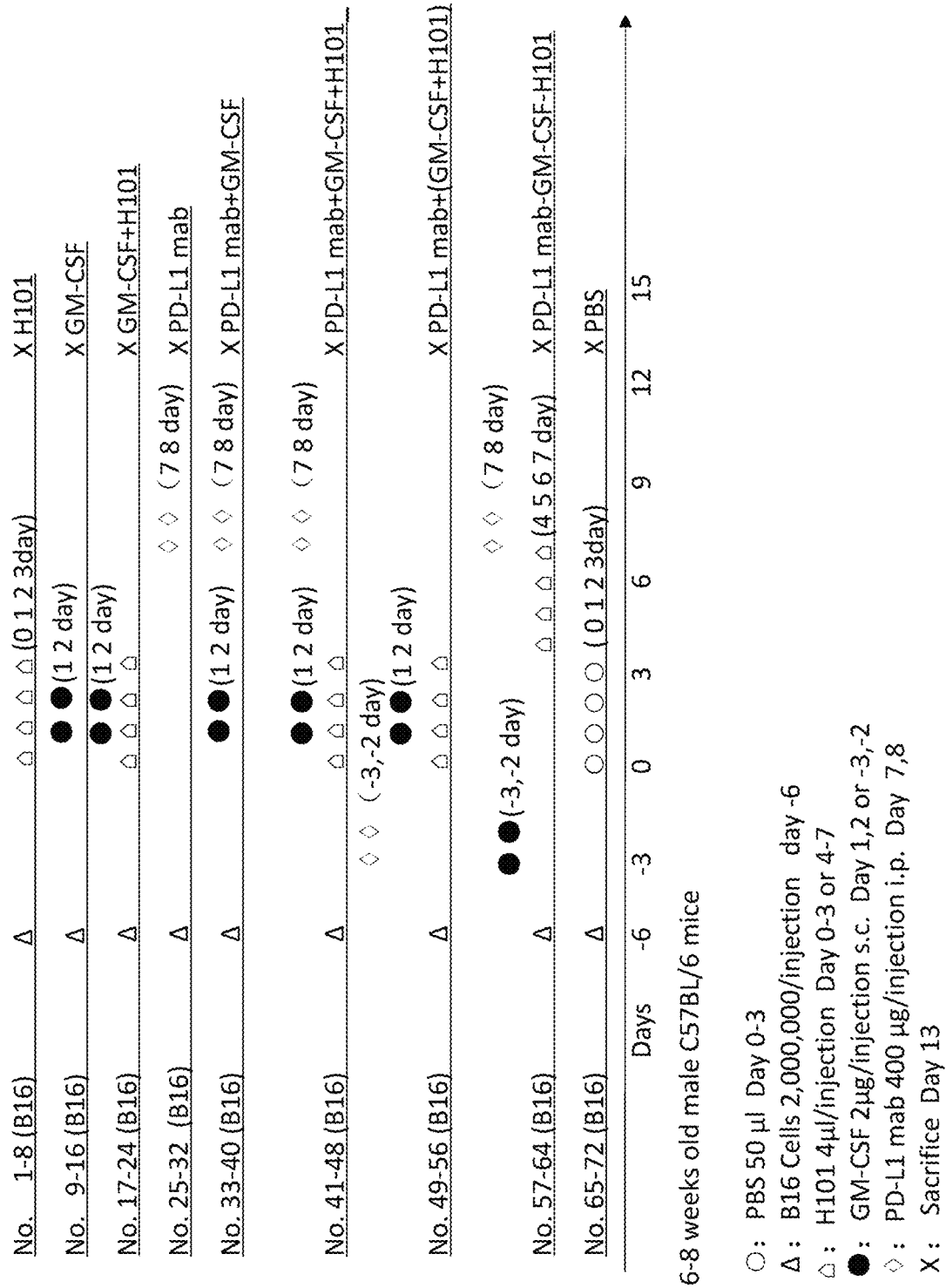
FIG. 17 is a flowchart showing the grouping and experiment design for systemic immunotherapeutic combination therapy in the Experimental example 5 of the present application.

72 male 6-8 weeks old C57BL/6 mice were subcutaneously (s.c.) inoculated on their back of the ribs with $2 \times 10^6$ B16 cells, and then monitored daily for tumor growth. These tumor-bearing animals were randomly numbered and then divided into 9 groups depended on the random number. Indicated groups were subjected to OVs (H101, $4 \times 10^9$ VPs) therapy i.t. and/or GM-CSF s.c. and/or PD-L1 mab (eBioscience, Cat#16-5982-85) i.p. or PBS (pH 7.4) only s.c. at indicated time points. After day 13, all animals were sacrificed and analyzed. Grouping and experiment design are illustrated in FIG. 17.

Figure 12A:
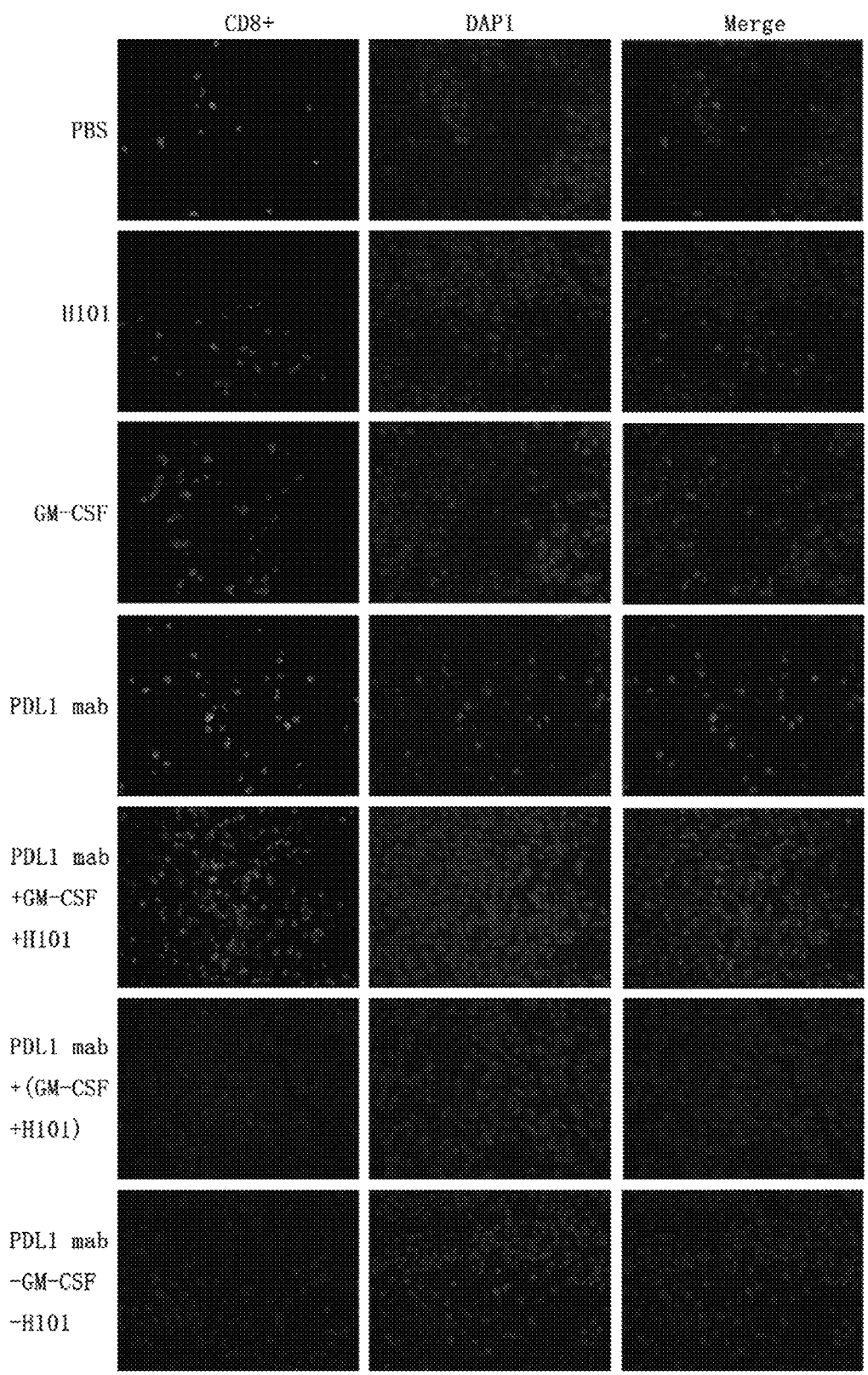
FIGS. 12A and 12B shows comparison of effect of the systemic assembling group and non-systemic assembling groups on $CD8^+$ TIL infiltration in tumor using Immunofluorescence analysis, which indicates that the systemic assembling induces the highest $CD8^+$ TIL infiltration through comparing the non-assembling groups and assembling group (PD-L1mab+GM-CSF+H101); wherein the results were presented as mean±SEM; *$p<0.05$; $p<0.01$; *$p<0.001$. Specifically.
Figure 12B:
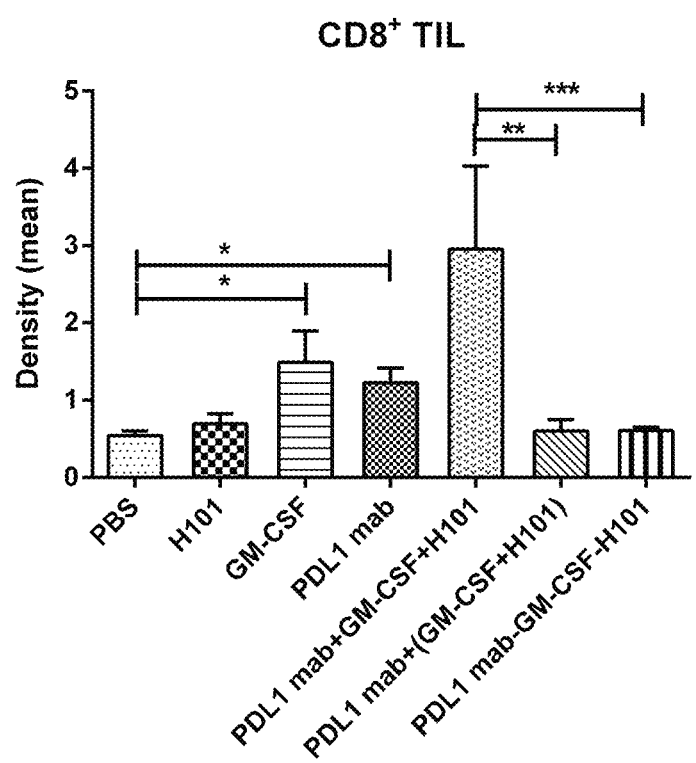

Immunofluorescence Analysis of CD8$^+$ TIL Infiltration in Tumor Using Systemic Immunotherapeutic Combination Therapy (for FIG. 12)

The level of CD8$^+$ TIL infiltration in tumor was determined by immunofluorescence staining. Briefly, tissue samples were fixed in 4% (v/v) Paraformaldehyde (Sangon Biotech, Shanghai, E672002) (PBS (pH 7.4) buffered) more than 24 hours, dehydrated in increasing concentrations of ethanol (70% (v/v) to 100% (v/v)), and processed for paraffin embedding and sectioning Immunofluorescence staining was performed on 4 µm thick sections of each tumor and there were at least three different samples for each group. After being dewaxed and rehydrated, sections were pretreatment with a microwave oven in citrate buffer (0.01 M, pH 6.0) to repair antigen. After 30 min incubation with 3% (w/v) BSA at room temperature, sections were incubated overnight at 4° C. with an anti-mouse monoclonal antibody CD8 (Clone CD8-144B; 1:50; Dako, Milan, Italy). These sections were then incubated for 50 minutes at room temperature with a FITC-conjugated anti-goat IgG secondary Ab (0.5 µg/40 µl) (Zymed Laboratories Inc., San Francisco, Calif., USA) to detect CD8. The nuclei were stained with DAPI for 10 min. After the treatment with antifade mounting medium, fluorescence signals were detected under fluorescence microscope (BX43, OLYMPUS). Fluorescence images were analyzed using Image-Pro Plus 6.0 software and the histogram was made by GraphPad Prism 5 software and $p<0.05$ was considered statistically significant.

Statistical Analysis (For All)

The sample size in all of in vitro and in vivo animal studies was selected according to the sample size estimate method ($\alpha=0.05$, power=90%) based on the mean and standard deviation (SD) in each group from preliminary experiments. The experimental cells or animals were randomly numbered and then divided into groups depended on the random number. All data were performed with a normal distribution test and results are expressed as mean±SEM. Analyses of different treatment groups were conducted using analysis of variance (ANOVA) and Student t test with the SPSS 16.0 software (SPSS, Chicago, Ill.). Histogram was made by GraphPad Prism 6.0.1 software. P<0.05 is considered statistically significant and asterisks denote significant differences between groups; *p<0.05; p<0.01; *p<0.001.

EXAMPLES

Experimental Example 1

Administration of H101 Increases the Release of Tumor Antigens at Tumor Site

Oncolytic virus (OV) H101 (Brand name: Oncorine) was already approved by CFDA in October, 2005 in CHINA, and its indication is Head and Neck Neoplasm. H101 possesses outstanding in vitro and in vivo oncolytic ability to most human tumor cells, while very weak oncolytic ability to most murine tumor cells. In this example, the weak oncolytic ability was utilized to trigger immune response in mice. On the other hand, to research the antitumor immune effect, the weak oncolytic ability was necessary to avoid CR (Complete Response) in early stage of animal model.

First of all, treatment of H101 faintly but significantly represses B16 murine melanoma cells in vitro after 4 days (FIG. 1).

Second, treatment of H101 to B16 cells induces early stage of apoptosis post 24 h and the percent of these cells have recovered after three days. (FIG. 2); Treatment of H101 to B16 cells induces late stage of apoptosis (necrosis) post 3-4 days in vitro (FIG. 3).

Moreover, the release of TSA (tumor specific antigen) caused by H101 was identified via murine HMGB1 ELISA. FIG. 4 shows that treatment of H101 to B16 cells causes oncolytic effects and release of tumor antigens post 3-4 days. Taken together, upon data illustrates that H101 could be assembled in our therapy as a TSA releasing agent and administration of H101 may induces the peak of TSA in vivo post 4 days.

Experimental Example 2

Administration of H101 Increases the Expression of MHCII at Tumor Site

MHC (major histocompatibility complex) class II molecules are a family of molecules normally found only on antigen-presenting cells such as dendritic cells, mononuclear phagocytes, some endothelial cells, thymic epithelial cells, and B cells, but may also be induced on other cells by interferon γ. Previous data shows that most OVs are potent inducers of MHC class I pathway-related molecules. Exposure of tumor cells to OVs in vitro enhances the expression of MHC class I molecules as compared with that observed in untreated cells. In this example, we discover that administration of H101 i.t. in vivo induces high expression of MHCII at tumor site (FIG. 5). Many tumor cells display constitutive or inducible levels of MHC class II, Unlike MHC class I, the clinical significance of MHC class II expression on tumor cells is still not clear. However, reasonably, up-regulation of MHC at the tumor site, should increase the level of antigen presentation and being recognized by immune cells; In one word, we utilize H101 to increase immunological recognition.

Experimental Example 3

Administration of Murine GM-CSF Induces the Expansion of DC in Spleen

To organic assemble the second agent, GM-CSF in our unique therapy, the time response curves of GM-CSF were verified in the healthy and immunocompetent C57BL/6 mouse model of B16 murine melanoma tumor. Previous data shows that GM-CSF mainly induces $CD11b^+$ DC in vivo. Our data shows that administration of murine GM-CSF s.c. induces expansion of $Ly-6G^+$ DC precursors at day 1 (FIG. 6) and $CD11b^+$ DC at day 2-4 (FIG. 7) post injection in spleen of healthy C57BL/6 mice. Moreover, administration of murine GM-CSF s.c. in B16 melanoma cell murine model induces up-regulation of $CD11b^+$ DC in spleen at Day 3.5 post injection (FIG. 8). Taken together, in our B16 murine model, GM-CSF induces DC expansion at day 2-4, the assembling of GM-CSF should be based on above data. (Note: The axis of abscissas in method is sorted by sequence of administration, however it is reversed and sorted by action time in the result figures)

Experimental Example 4

Administration of Murine PD-L1 Antibodies i.p. Represses Tumor Growth In Vivo

To increase the level and improve the function of the effector cells ($CD8^+$ T cells) in tumor site, immune checkpoint inhibitors were utilized in this example. Totally three immune checkpoint antibodies were investigated, two of them are PD-1 antibodies (RMP1-14 and J43) and another one is PD-L1 antibody (MIH5). FIG. 9 shows that single injection of murine PD-L1 or PD-1 mab i.p. in B16 melanoma murine model represses tumor growth, and the PD-L1 mAb (MIH5) exhibited the best efficacy. Thus, we engage the PD-L1 mAb (MIH5) to improve the activity of T cells. The assembling of PD-L1 mab is based on nature of adoptive immune response.

Experimental Example 5

Figure 11:
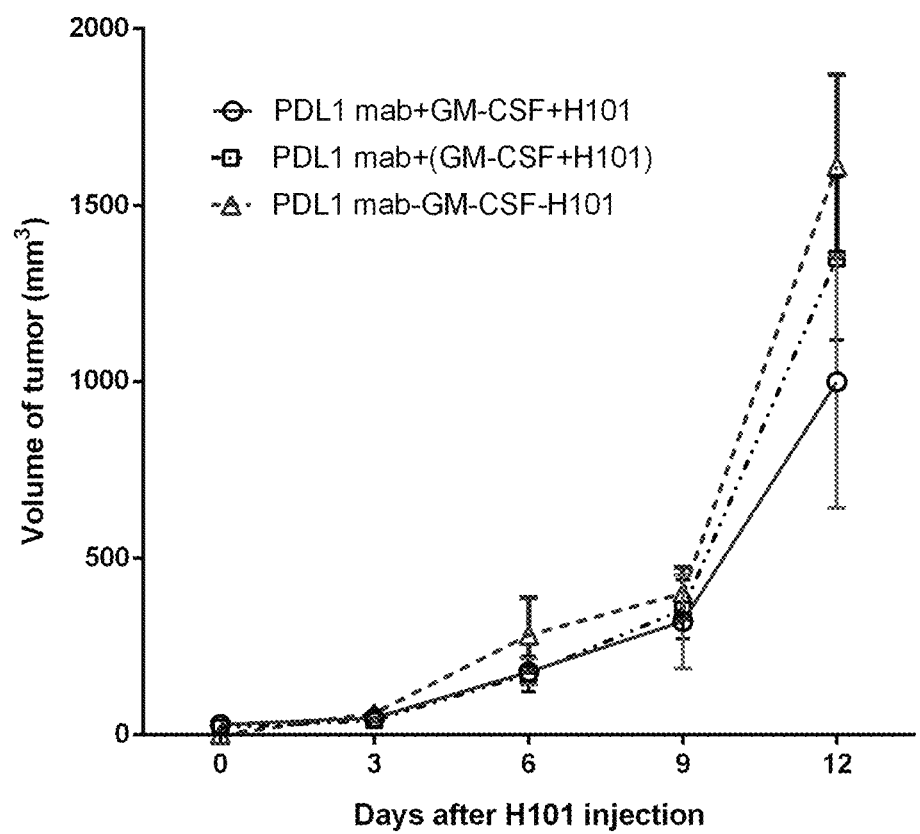
FIG. 11 shows comparison of the antitumor efficacy of the non-assembling groups and assembling group (PD-L1 mab+GM-CSF+H101); wherein the results were presented as mean±SEM.

Individualized Systemic Immunotherapeutic Method Gains Maximized Antitumor Efficacy Based on our data and concept, some systemic assembling was investigated on B16 melanoma murine model. We considers that TSAs should be released by H101 first of all (Day 4 post administration of H101), and then the peak of TSAs could be matched with the peak of DC (Day 2-3 post administration of GM-CSF). Finally, the peak of mature DC (almost three days after expansion) would be matched with the peak of activated T cells (considering day 1 post administration of PD-L1 mab). For example, the antitumor efficacies of single reagent, double reagents, and triple reagents were compared. More important, the antitumor efficacies of the systemic assembling (PD-L1 mab+GM-CSF+H101) and other two non-systemic assembling (PD-L1 mab+(GM-CSF+H101), PD-L1 mab−GM-CSF−H101) were compared. FIG. 10 shows that comparing to single reagent or double reagents, the triple reagents (PD-L1 mab+GM-CSF+H101) exhibited the best antitumor efficacy at day 9. Comparing the non-assembling groups and assembling group (PD-L1 mab+GM-CSF+H101), administration of PD-L1 mab ahead of original assembling time (PD-L1 mab+(GM-CSF+H101)) attenuates the antitumor efficacy (FIG. 11). Critically, the assembling group (PD-L1 mab+GM-CSF+H101) dramatically induced $CD8^+$ TIL infiltration in injection site, which is well-recognized indicator for antitumor immunotherapy (FIG. 12). This is a very potent proof to verify the efficacy of our individualized systemic immunotherapeutic method. Since the B16 cells grow very quickly in immunocompetent animal, it is impossible to get CR by this model, but based on these animal studies, the theory of assemble of immune process was well verified.

CONCLUSION

Immunotherapy for the treatment of cancer is rapidly evolving from therapies that globally and non-specifically simulate the immune system to more targeted activation of individual components of the immune system. However, up to date, those combination therapies were not able to combine all components systemically.

To solve the above-mentioned problem, the present invention provides an in vivo individualized systemic immunotherapeutic method as described above, and in the examples, three independent reagents were selected and assembled together according to the unique Systemic Immunotherapeutic Method. Briefly, the systemic immunotherapeutic pipeline was assembled based on the feature of each Immunotherapeutic reagents and the nature of adaptive antitumor immune response.

Here, the immunotherapeutic method is assembled via three reagents: H101, GM-CSF, PD-L1 mAb.

(1) Oncolytic virus (OV) H101 is a recombinant human type-5 adenovirus (Ad5) in which the gene encoding the 55 kDa E1B protein responsible for p53-binding and inactivation has been deleted to confer p53-selective replication of oncolytic viruses inducing accumulation of p53 leading to direct and selective cytotoxicity in tumor cells during replication. The H101 virus produced by Shanghai Sunway Biotech also contains a deletion of a 78.3-85.8 μm gene segment in the E3 region. The E3 region is responsible for the inhibition of host immunity, which enhances virus replication and spread in tumor cells. Moreover, H101 Injection (Brand name: Oncorine) got NDA of national class I biological products in October, 2005 in CHINA. H101 selectively replicate and kill cancer cells and spread within the tumor, while not harming normal tissue.

As the first agent in this therapy, H101 lyses tumor cells and consequently releases the tumor specific antigen (TSA), priming the adaptive antitumor immune responses. The time response curves are disclosed, and optimized administration is assembled.

(2) Granulocyte-macrophage colony-stimulating factor (GM-CSF), also known as colony stimulating factor 2 (CSF2), is a monomeric glycoprotein secreted by macrophages, T cells, mast cells, NK cells, endothelial cells and fibroblasts that functions as a cytokine. Furthermore, Dendritic cells (DC) are potent APCs that can be characterized in the murine spleen as $CD11b^{high}$ or $CD11c^{high}$. Administration of murine GM-CSF to mice led to an up-regulation of $CD11b^{high}$ but not $CD11c^{high}$ DC. In the immunotherapeutic method, murine GM-CSF was engaged as a critical element to induce APCs ($CD11b^{high}$ DCs). The time response curves are disclosed, and optimized administration are assembled.

(3) Programmed death-ligand 1 (PD-L1) also known as cluster of differentiation 274 (CD274) or B7 homolog 1 (B7-H1) is a 40 kDa type 1 transmembrane protein that has been illuminated to play a major role in suppressing the immune system during particular events such as cancer, and is expressed on a majority of leukocytes including T, B, NK, DC and tumor cells. Normally the immune system reacts to foreign antigens where there is some accumulation in the lymph nodes or spleen which triggers a proliferation of antigen-specific $CD8^+$ T cell. The formation of PD-1 receptor/PD-L1 or B7-1 receptor/PD-L1 ligand complex transmits an inhibitory signal which reduces the proliferation of these $CD8^+$ T cells at the lymph nodes, and supplementary to that PD-1 is also able to control the accumulation of foreign antigen specific T cells in the lymph nodes through apoptosis which is further mediated by a lower regulation of the gene Bcl-2. Engagement of PD-L1 with its receptor PD-1 on T cells delivers a signal that inhibits TCR-mediated activation of IL-2 production and T cell proliferation. PD-L1 binding to PD-1 also contributes to ligand-induced TCR down-modulation during antigen presentation to naive T cells, by inducing the up-regulation of the E3 ubiquitin ligase CBL-b. Data shows that upregulation of PD-L1 on tumor cells may allow cancers to escape from the host immune system. In another word, PD-L1 on tumor cells may suppress antitumor $CD8^+$ T cells. Following the FDA approval of a number of immune checkpoint inhibitors for cancer treatment, the PD-L1 functional antibodies come to great success.

Here, the functional grade purified anti-mouse CD274 (B7-H1) monoclonal antibody was used as a blocking antibody, to block the PD-1/PD-L1 immune checkpoint. The response curves of different immune checkpoint inhibitors are disclosed, and optimized administration is assembled.

Our data shows that organic/systemic combination of individual components via Individualized Systemic Immunotherapeutic Method would trigger the antitumor immune response and maximize the antitumor efficacy. Here, systemic integration of regimen of individual components is a unique method according to the present invention.

Clinical Trial Example 1

Clinical trial example 1 was a statistical experimental example regarding multiple patients and it was an exploratory clinical trial in patients with late-stage non-small cell lung cancer (NSCLC). The included patients were those who had inoperable stage III or IV cancer or recurrent stage III or IV cancer after surgery or chemotherapy, as well as a small proportion of patients who refused to receive chemotherapy or radiotherapy.

The therapeutic regimen adopted in clinical trial example 1 was: CT-guided percutaneous intratumoral injection of H101 and IL-2 plus application of topical heat (42.5° C.) plus chemotherapy.

The results of the therapeutic regimen in clinical trial example 1 are listed in Table 2.

TABLE 2

The statistical results of clinical trial example 1

| Sex | Age | Diagnosis | Time of diagnosis | Time of H101 treatment | Efficacy | ST | TTP |
|---|---|---|---|---|---|---|---|
| Male | 45 | Adenocarcinoma (IV) | 2002.10 | 2002.11 | PR | 13 months | 13 months |
| Male* | 75 | Adenocarcinoma (IIIb) | 2002.11 | 2002.11 | SD | 5 months | 5 months |
| Male* | 69 | Adenocarcinoma (IV) | 2002.12 | 2003.1 | PR | >23 months | 23 months |
| Male* | 75 | Adenocarcinoma (III) | 2002.5 | 2003.2 | MR | 14 months | 14 months |
| Female | 47 | Adenocarcinoma (IV) | 2003.2 | 2003.2 | MR | >21 months | 20 months |
| Male | 71 | squamous cell carcinoma (IIb) | 2003.3 | 2003.3 | SD | 12 months | 12 months |
| Male | 75 | NSCLC (IIIa) | 2003.3 | 2003.3 | SD | >20 months | 16 months |
| Male | 46 | Adenocarcinoma (IV) | 2003.3 | 2003.4 | PR | >19 months | 9 months |
| Male | 47 | squamous cell carcinoma (IIIa) | 2003.10 | 2003.11 | PD | >11 months | 5 months |
| Female | 72 | NSCLC (IV) | 2004.8 | 2004.9 | SD | >3 months | >3 months |

Wherein, *indicates that the patient didn't receive chemotherapy. The abbreviations in the table are explained as follows:
CR, Complete Response: It means that the tumor is completely gone.
PR, Partial Response: It means that the tumor size is reduced by more than 50%.
MR, Minor Response: It means remission and the tumor size is reduced by more than 25% but less than 50%.
SD, Stable Disease: It means that the disease is stable and the tumor size is reduced by less than 25% or increases by less than 25%.
PD, Progressive Disease: It means progression and the tumor size increases by more than 25% or new foci appear.
TTP, Time to progression: It means the time from treatment to progression.
ST, Survival time: It means how long the patient survives.

It needs to be noted that, in the above explanation of the abbreviations in Table 2, the tumor size is defined as the product of the two largest perpendicular diameters of the tumor.

As shown in Table 2, a total of 10 patients with late-stage NSCLC were included into the exploratory clinical trial and given the combination therapy of oncolytic therapy using H101, immunotherapy and chemotherapy as first-line treatment, and the response rate (RR) was 30%, which was comparable to the response rate in the routine treatment using chemotherapy alone. Among these 10 patients, 9 patients achieved SD or better efficacy, 7 patients achieved a TTP of more than 9 months, and 7 patients achieved an ST of more than 11 months, and all these results were superior to those of chemotherapy alone.

It needs to be noted that in clinical trial example 1, most of the patients who underwent chemotherapy received the chemotherapeutic agents prior to injection of H101. Surely, in the practice, chemotherapy can be given simultaneously with injection of H101 or after injection of H101, however, the chemotherapeutic agents will harm the immune system, and the therapeutic effect will not be as significant as that in this embodiment.

The results of clinical trial example 1 were compared to that of the 5 typical chemotherapy studies with large sample sizes, and the results are shown in Table 3.

TABLE 3

Comparison of the results between clinical trial example 1 and the 5 typical chemotherapy studies with large sample sizes

|  | The averages in the 5 typical chemotherapy studies with large sample sizes (minimum value-maximum value) | Clinical trial example 1 |
| --- | --- | --- |
| Objective response rate (%) | 21 (17-37) | 30 (3/10) |
| Time to progression (month) | 4.5 (3.5-5.5) | >11.9 (>5-21) |
| Median survival time (month) | 8.8 (6.7-11.3) | >13 |
| 1-year survival rate (%) | 36 (27-46) | 70 |

Wherein, the therapeutic regimen adopted in clinical trial example 1 was: H101+Chemotherapy+topical heat+IL-2. The 5 typical studies with large sample sizes are ECOG1594, SWOG, Italian Lung Cancer trial, EORTC08975, and Tax326.

It is shown in Table 3 that the average time to progression was 12 months, the median survival time was 13 months, and the 1-year survival rate was 70% in clinical trial example 1. While the time to progression, median survival time and 1-year survival rate in the internationally renowned 5 typical chemotherapy studies with large sample sizes were 4.5 months, 8.8 months and 36%, respectively. Therefore, the anti-tumor therapeutic method of this invention has significantly superior efficacy compared to that of the 5 typical chemotherapy studies with large sample sizes.

It is understandable that the simultaneous occurrence of topical heat-induced expression of HSP and lysis of the tumor cells ensures overall presentation of tumor-specific antigens released from the tumor cells to the immune system of human body by HSPs, instead of single presentation of some type of tumor-specific or tumor-associated antigens; therefore, improved efficacy can be achieved in individual patients.

It can be further understood that the whole therapeutic process in clinical trial example 1 occurred in vivo and the included patients could receive the same drugs and procedures during the course of treatment for individualized effects; therefore, this therapeutic method is not only easy to carry out, but can also improve the individual patient-specific immune responses against multiple tumor antigens.

Therefore, it can be concluded from clinical trial example 1 that the anti-tumor therapeutic method of the present invention can be widely used in clinical practice.

Clinical Trial Example 2

Patient No. 1 was a 45-year-old male. He experienced repeated episodes of cough without apparent cause in September 2002. The CT scan performed in October 2002 revealed: a space-occupying lesion in the right middle lobe of the lung; bilateral diffuse miliary foci; mediastinal lymph node enlargement; right-sided moderate pleural effusion. The result of the pathological examination of pleural effusion carried out in October 2002 was: adenocarcinoma cells. The patient was diagnosed with bilateral alveolar cell carcinoma; adenocarcinoma of the right lung. Staging: T4N3M1/IV (stage IV). The KPS (Karnofsky Performance Status Scale) score was 80.

The patient received the anti-tumor therapy of the present invention since October 2002. The detailed therapeutic regimen was: chemotherapy+H101+IL-2+topical heat, wherein the chemotherapeutic agents were Gemzar 1.6 mg and Cisplatin 100 mg; H101 and IL-2 were administrated into the pleural cavity through percutaneous injection; topical heat was applied to the chest area at 42.5° C. The chest X-ray performed at 16 days after initial treatment suggested: the lung markings are clear; the costophrenic angles are shown; pleural effusion has basically disappeared. After the first course of treatment ended in December 2002, the symptoms including chest tightness and cough were improved; thoracentesis was performed and only 3 to 4 ml of fluid was obtained (it was 300 ml before the treatment). The CT scan showed: significant decrease in the number of diffuse miliary foci; the volume of pleural effusion has decreased; the lung markings are clear. After the second course of treatment ended in January 2003, the CT scan indicated: pleural effusion has disappeared; the number of diffuse miliary foci has decreased by more than 70% compared to the CT findings before the treatment; the lung markings are clear; the symptom of cough has been improved significantly. However, chemotherapy had to be stopped due to low platelet count (1500). The patient received Taxotere plus Cisplatin before the third course of treatment began in March 2003. The fourth course of treatment for the patient started in April 2003. A molecular targeting agent for tumor, Iressa, was used throughout the entire treatment.

A partial response (PR) was obtained in patient No. 1 following the anti-tumor therapy of the present invention; the survival time for patient No. 1 was 13 months.

From the results of the above experiment, it can be concluded that significant efficacy can be achieved with the anti-tumor therapeutic method of the present invention. The inventors speculate that this significant efficacy may be the result of synergism between the molecular targeting agent for tumor, i.e., Iressa and H101, and the presumed mechanisms of this synergism are described below, including but not limited to:

1. H101 has dual functions after entering into the tumor cells, that is (1) oncolytic viral replication through activation of the PI3K/ATK (phosphoinositide 3-kinase/activated tyrosine kinase) pathway and RAS/RAF pathway; (2) Lysis of tumor cells. However, the PI3K/ATK pathway and RAS/RAF pathway can protect the tumor cells, stimulate cell division and proliferation, and prevent apoptosis. Therefore, it will not be easy to kill the tumor cells. However, Iressa can block the above two signaling pathways, so when it is applied during the cell lysis period after replication of H101, the lytic effect of H101 against tumor cells will be enhanced.

2. H101 can replicate inside tumor cells and fight for the resources with them, which exerts a selection pressure on the tumor cells, i.e. the tumor cells with stronger proliferative abilities will have a selective advantage; but these tumor cells may also rely on activation of some signaling pathways for proliferation, among which the PI3K/ATK and RAS/RAF signaling pathways are two main pathways. Therefore, application of H101 may increase the sensitivity of tumor cells to Iressa, thus enhance its tumor killing activity. Furthermore, E1A-mediated down-regulation of EGFR can induce tumor cell apoptosis, which affects the same pathways as Iressa does, resulting in synergistic killing of tumor cells.

3. T cells play an important role in the regulation of the immune responses to tumor cells, which induce apoptosis and lysis of tumor cells via the Fas/FasL pathway, the perforin/granzyme pathway and TNFs. However, the PI3K/ATK and RAS/RAF pathways can prevent the apoptosis of cells and protect tumor cells from being killed by lymphocytes. Therefore, Iressa-mediated inhibition of these two pathways may enhance the sensitivity of tumor cells to T cell-mediated killing, so that the systemic therapeutic effect of immunotherapy can be improved.

4. Iressa is highly selective and has no apparent effect on the immune system, and it can decrease tumor burden, therefore, a synergistic effect can be achieved between lysis of tumor cells by H101 and inhibition of tumor growth by Iressa.

Clinical Trial Example 3

Patient No. 2 was a 47-year-old female. She started experiencing dry coughs in February 2003, which worsened in March, but there were no symptoms like expectoration of phlegm, hemoptysis, or fever. The CT scan performed in March 2003 suggested: a mass measuring about 2×3×2 cm at the left hilus of lung; a mass measuring 4.2×4.1 cm at the lower lobe of the left lung. Diagnosis: adenocarcinoma of the left lung. Staging: T4N2M1/IV (Stage IV). KPS score: 80.

Patient No. 2 started receiving the CHINA anti-tumor therapy of the present invention in March 2003. The detailed therapeutic regimen was: chemotherapy+H101+IL-2+GM-CSF+topical heat, wherein, the chemotherapeutic agents were Gemzar 1.6 mg and Cisplatin 100 mg; H101, IL-2 and GM-CSF were administrated into the pleural cavity through percutaneous injection; topical heat was applied to the chest area at 42.5° C.

Cough relief was observed after the first course of treatment ended. The patient received the second course of treatment in April 2003, the third course of treatment in June 2003 and the fourth course of treatment in August 2003.

Significant decrease of tumor size was observed in Patient No. 2 after four courses of treatment, and liquefactive necrosis could be seen inside the tumors. The symptoms such as cough and chest tightness were significantly relieved.

A partial response (PR) was obtained in patient No. 2 following the anti-tumor therapy of the present invention; the survival time for patient No. 2 was more than 20 months.

The treatment procedures and results regarding Patient No. 1 and Patient No. 2 suggest that the efficacy of the anti-tumor therapeutic method of the present invention is superior to that of the anti-tumor strategies in the prior art.

It needs to be noted that the above examples are just some preferred embodiments of the present invention. Improvements or modifications may be practiced within the scope of the basic mechanisms of this invention by those skilled in the art, and such improvements and modifications are considered to be within the scope of the present invention.

The invention claimed is:

1. A tumor-specific antigen anti-tumor therapeutic method, comprising performing a protocol including steps of:
   (1) increasing release amount of tumor antigens at a tumor site where treatment is required in a tumor patient;
   (2) at the tumor site, increasing level of proteins capable of adhering to and/or wrapping the tumor antigens;
   (3) at the tumor site, increasing level of dedicated antigen-presenting cells involved in immunity, and establishing, between the dedicated antigen-presenting cells and immune effector cells, a connection capable of activating the immune effector cells; and
   (4) at the tumor site, increasing level of the immune effector cells and improving function thereof, thus establishing a connection between the immune effector cells and target cells, resulting in killing of the target cells;
   wherein the release amount of the tumor antigens in step (1), the level of the proteins capable of adhering to and/or wrapping the tumor antigens in step (2), the level of the dedicated antigen-presenting cells involved in immunity and the connection between the dedicated antigen-presenting cells and the immune effector cells in step (3), and the level and function of the immune effector cells in step (4) each reaches a maximum value at a respective time which overlaps with each other maximally, as well as at a respective site which overlaps with each other maximally,
   wherein:
   step (1) and step (2) of the protocol comprises applying oncolytic virus H101 to the tumor site on day 0, day 1, day 2, and day 3 of the protocol,
   step (3) of the protocol comprises administering GM-CSF to the tumor patient on days 1 and 2 of the protocol, and
   step (4) of the protocol comprises administering PD-L1 antibodies to the tumor patient on days 7 and 8 of the protocol.

2. The therapeutic method according to claim 1, wherein the therapeutic method comprises a step of chemotherapy and/or radiotherapy for said tumor patient.

3. The therapeutic method according to claim 2, wherein an agent used for said chemotherapy includes Vinorelbine, Cisplatin, Adriamycin, Gemzar, or 5-fluorouracil.

4. The therapeutic method according to claim 2, wherein said step of chemotherapy and/or radiotherapy is performed prior to the step (1), (2), (3) and (4).

5. The therapeutic method according to claim 1, wherein the therapeutic method comprises a step of administration of a molecular targeting agent for tumor to said tumor patient.

6. The therapeutic method according to claim 5, wherein said molecular targeting agent for tumor includes monoclonal antibodies and/or small-molecule compounds which aim at specific targets on tumor cells.

7. The therapeutic method according to claim 6, wherein said monoclonal antibodies and/or small-molecule compounds which aim at specific targets on tumor cells include: Tamoxifen, Toremifene, Anastrozole, exemestane, Letrozole, Imatinib Mesylate, Vemurafenib, Rituximab, Ofatumumab, Tositumomab Ibritumomab Tiuxetan, Brentuximab Vedotin, Alemtuzumab, Ipilimumab, Gefitinib, Erlotinib, Cetuximab, Panitumumab, Crizotinib, Trastuzumab, Lapatinib, Vorinostat, Romidepsin, Denileukin Diftitox, Temsirolimus, Everolimus, Bortezomib, Alitretinoin, Tretinoin, Bexarotene, Bevacizumab, Sorafenib, Sunitinib, Pazopanib, Dasatinib, Nilotinib, and/or Vandetanib.

8. The therapeutic method according to claim 1, wherein the therapeutic method comprises giving nutrition support to said tumor patient during entire treatment course, and the nutrition given by said nutrition support includes amino acids, fats and trace elements.

9. The therapeutic method according to claim 1, wherein an agent which can induce tumor cell necrosis to said tumor site is administered, and is selected from absolute ethyl alcohol, acetic acid, hot saline water, or hot distilled water.

* * * * *